US012135283B2

(12) United States Patent
Yamakawa et al.

(10) Patent No.: US 12,135,283 B2
(45) Date of Patent: Nov. 5, 2024

(54) TISSUE IDENTIFICATION DEVICE, TISSUE IDENTIFICATION SYSTEM, METHOD OF IDENTIFYING TISSUE, AND STORAGE MEDIUM

(71) Applicants: National Institutes for Quantum Science and Technology, Chiba (JP); Light Touch Technology Incorporated, Osaka (JP)

(72) Inventors: Koichi Yamakawa, Kyoto (JP); Makoto Aoyama, Kyoto (JP); Takamitsu Morioka, Chiba (JP); Tatsuhiko Imaoka, Chiba (JP); Kanade Ogawa, Osaka (JP)

(73) Assignees: National Institutes for Quantum Science and Technology, Chiba (JP); Light Touch Technology Incorporated, Osaka (JP)

( * ) Notice: Subject to any disclaimer, the term of this patent is extended or adjusted under 35 U.S.C. 154(b) by 975 days.

(21) Appl. No.: 17/053,274

(22) PCT Filed: Apr. 26, 2019

(86) PCT No.: PCT/JP2019/017863
§ 371 (c)(1),
(2) Date: Nov. 5, 2020

(87) PCT Pub. No.: WO2019/216260
PCT Pub. Date: Nov. 14, 2019

(65) Prior Publication Data
US 2021/0085186 A1    Mar. 25, 2021

(30) Foreign Application Priority Data

May 9, 2018 (JP) .................................. 2018-090871

(51) Int. Cl.
A61B 1/00 (2006.01)
A61B 1/04 (2006.01)
(Continued)

(52) U.S. Cl.
CPC ......... *G01N 21/39* (2013.01); *A61B 1/00004* (2013.01); *A61B 1/044* (2022.02);
(Continued)

(58) Field of Classification Search
None
See application file for complete search history.

(56) References Cited

U.S. PATENT DOCUMENTS 5,733,739 A    3/1998  Zakim et al.
2002/0164810 A1  11/2002  Dukor et al.
(Continued)

FOREIGN PATENT DOCUMENTS

CN    1264314 A    8/2000
CN    1397794 A    2/2003
(Continued)

OTHER PUBLICATIONS

TIPO, Office Action for corresponding Taiwanese Patent Application No. 108120531, dated Oct. 4, 2022, 25 pages.
(Continued)

*Primary Examiner* — Joel Lamprecht
*Assistant Examiner* — Ashish S Jasani
(74) *Attorney, Agent, or Firm* — NK Patent Law

(57) ABSTRACT

A control section as a tissue identification device includes: an absorbance ratio calculating section configured to calculate the ratio of an absorbance indicated by a transmitted portion of first inspection light transmitted through biological tissue to an absorbance indicated by a transmitted portion of second inspection light transmitted through the biological tissue; and an identification information generating section
(Continued)

configured to generate identification information indicative of the type or state of the biological tissue by determining within which of a plurality of preset numerical ranges the ratio falls.

19 Claims, 27 Drawing Sheets

(51) Int. Cl.
  *A61B 1/06* (2006.01)
  *A61B 5/00* (2006.01)
  *A61B 5/06* (2006.01)
  *A61B 5/20* (2006.01)
  *G01N 21/39* (2006.01)
(52) U.S. Cl.
  CPC ............ *A61B 1/063* (2013.01); *A61B 5/0079* (2013.01); *A61B 5/0084* (2013.01); *A61B 5/0091* (2013.01); *A61B 5/06* (2013.01); *A61B 5/201* (2013.01); *A61B 5/416* (2013.01); *A61B 5/417* (2013.01); *A61B 5/4244* (2013.01); *A61B 5/4504* (2013.01); *A61B 5/4519* (2013.01); *A61B 5/742* (2013.01)

(56) References Cited

U.S. PATENT DOCUMENTS

| | | | |
|---|---|---|---|
| 2004/0068163 | A1 | 4/2004 | Ruchti et al. |
| 2004/0127777 | A1 | 7/2004 | Ruchti et al. |
| 2007/0282190 | A1 | 12/2007 | Dekel et al. |
| 2008/0024788 | A1 | 1/2008 | Shimizu et al. |
| 2009/0198113 | A1 | 8/2009 | Rensen et al. |
| 2010/0069723 | A1 | 3/2010 | Islam |
| 2011/0216309 | A1 | 9/2011 | Tezuka et al. |
| 2012/0052063 | A1* | 3/2012 | Bhargava ............ G06F 18/2415 382/128 |
| 2012/0253335 | A1 | 10/2012 | Flynn |
| 2015/0198793 | A1* | 7/2015 | Kosanic ............ G02B 23/2476 600/116 |
| 2016/0224016 | A1 | 8/2016 | Price et al. |
| 2016/0377634 | A1 | 12/2016 | Ochiai |
| 2018/0000386 | A1 | 1/2018 | Yamakawa |
| 2018/0116567 | A1 | 5/2018 | Jeda et al. |
| 2018/0306710 | A1* | 10/2018 | Phillips ................ G01N 21/314 |
| 2019/0049468 | A9 | 2/2019 | Ochiai |
| 2019/0120753 | A1* | 4/2019 | Prater .................... G01N 21/59 |
| 2019/0358348 | A1* | 11/2019 | Abbaci .............. G01N 21/6458 |
| 2020/0069165 | A1* | 3/2020 | Thomson ................. A61B 1/06 |
| 2021/0038125 | A1 | 2/2021 | Yamakawa |

FOREIGN PATENT DOCUMENTS

| | | |
|---|---|---|
| CN | 101103905 A | 1/2008 |
| CN | 106104259 A | 11/2016 |
| CN | 107427266 A | 12/2017 |
| JP | 09219563 A | 8/1997 |
| JP | 11507133 A | 6/1999 |
| JP | 2004515759 A | 5/2004 |
| JP | 2006191937 A | 7/2006 |
| JP | 2007259987 A | 10/2007 |
| JP | 2010227558 A | 10/2010 |
| JP | 2011101763 A | 5/2011 |
| JP | 2013195522 A | 9/2013 |
| JP | 2015102542 A | 6/2015 |
| JP | 2017064405 A | 4/2017 |
| JP | 2017074177 A | 4/2017 |
| TW | I324686 B | 5/2010 |
| WO | 1997018566 A1 | 5/1997 |
| WO | 2011151825 A2 | 12/2011 |
| WO | 2013139348 A1 | 9/2013 |
| WO | 2015097089 A1 | 7/2015 |
| WO | WO-2016174441 A1 * | 11/2016 ........... A61B 5/0075 |
| WO | 2017072320 A1 | 5/2017 |

OTHER PUBLICATIONS

ISA/JP, International Search Report for corresponding PCT Patent Application No. PCT/JP2019/017863, mailed Jul. 16, 2019, 5 pages.
WIPO, International Preliminary Report on Patentability for corresponding PCT Patent Application No. PCT/JP2019/017863, mailed Nov. 19, 2020, 19 pages.
JPO, Office Action for corresponding Japanese Patent Application No. 2020-500748, mailed Mar. 17, 2020, 15 pages.
JPO, Final Office Action for corresponding Japanese Patent Application No. 2020-500748, mailed Jul. 28, 2020, 15 pages.
EPO, Extended European Search Report for corresponding European Patent Application No. 19799119.3, mailed May 27, 2021, 5 pages.
Lu Zukang et al., "Optical Properties of Normal and Carcinomatous Human Lung Tissue at 632.8nm of a He—Ne Laser", Chin. J. Laser Med. Surg. 7 (2), p. 63-68, 1998.
CNIPA, First Office Action for corresponding Chinese Patent Application No. 201980045891.3 issued on Jan. 9, 2024, 13 pages.

* cited by examiner

FIG. 21
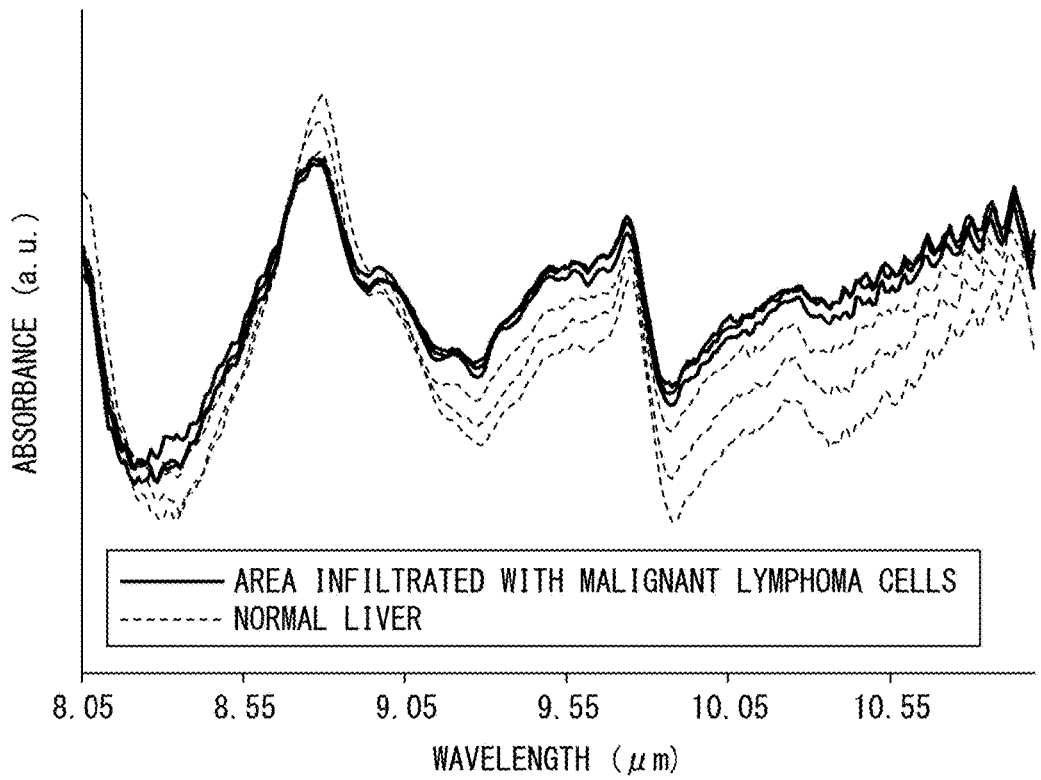
(a)
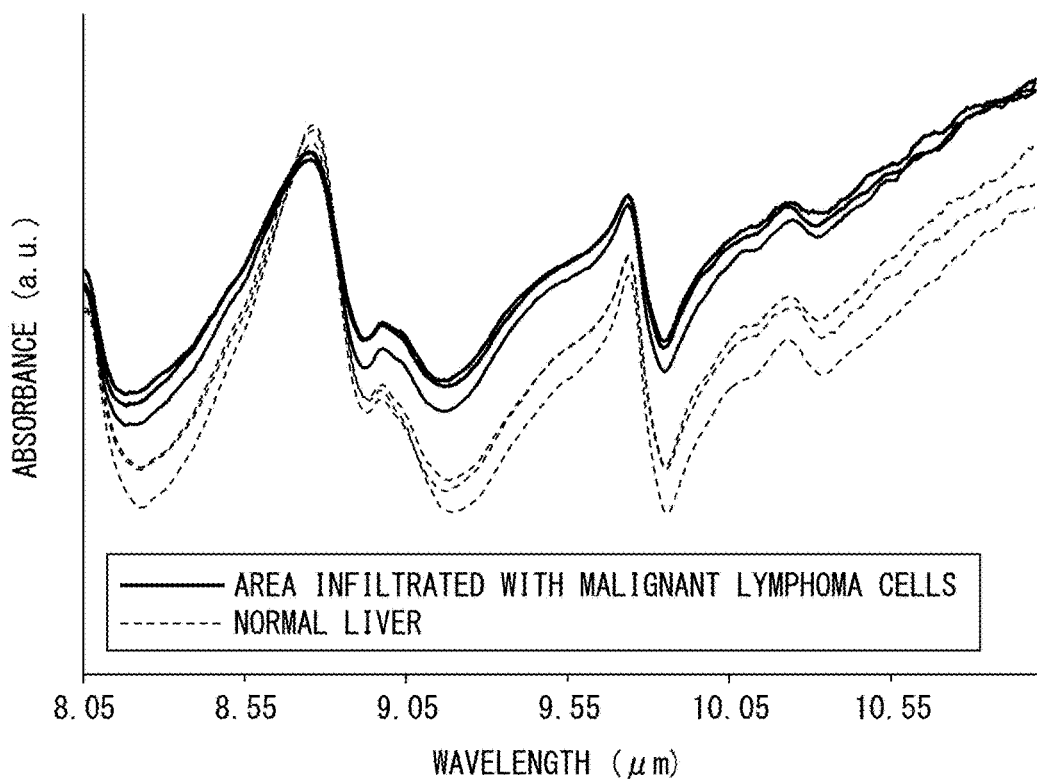
(b)

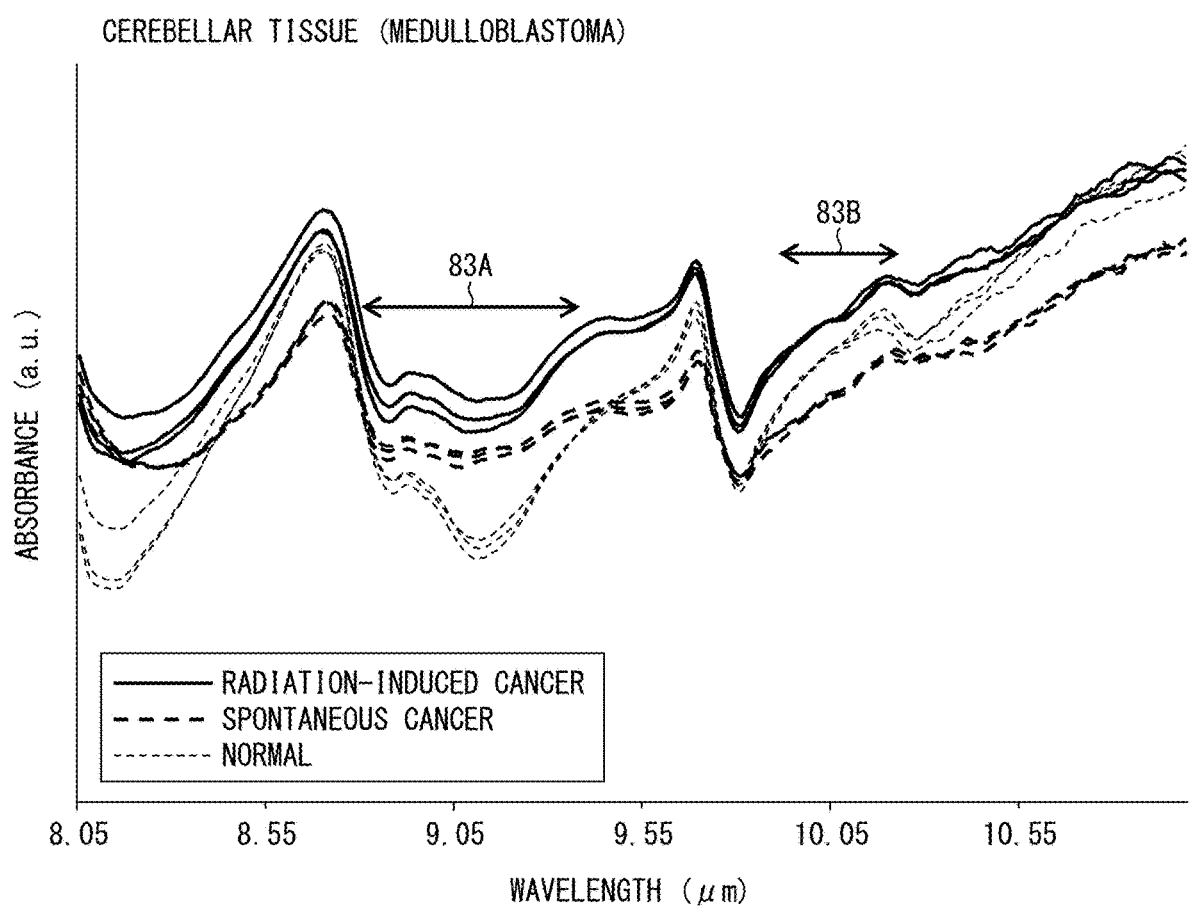

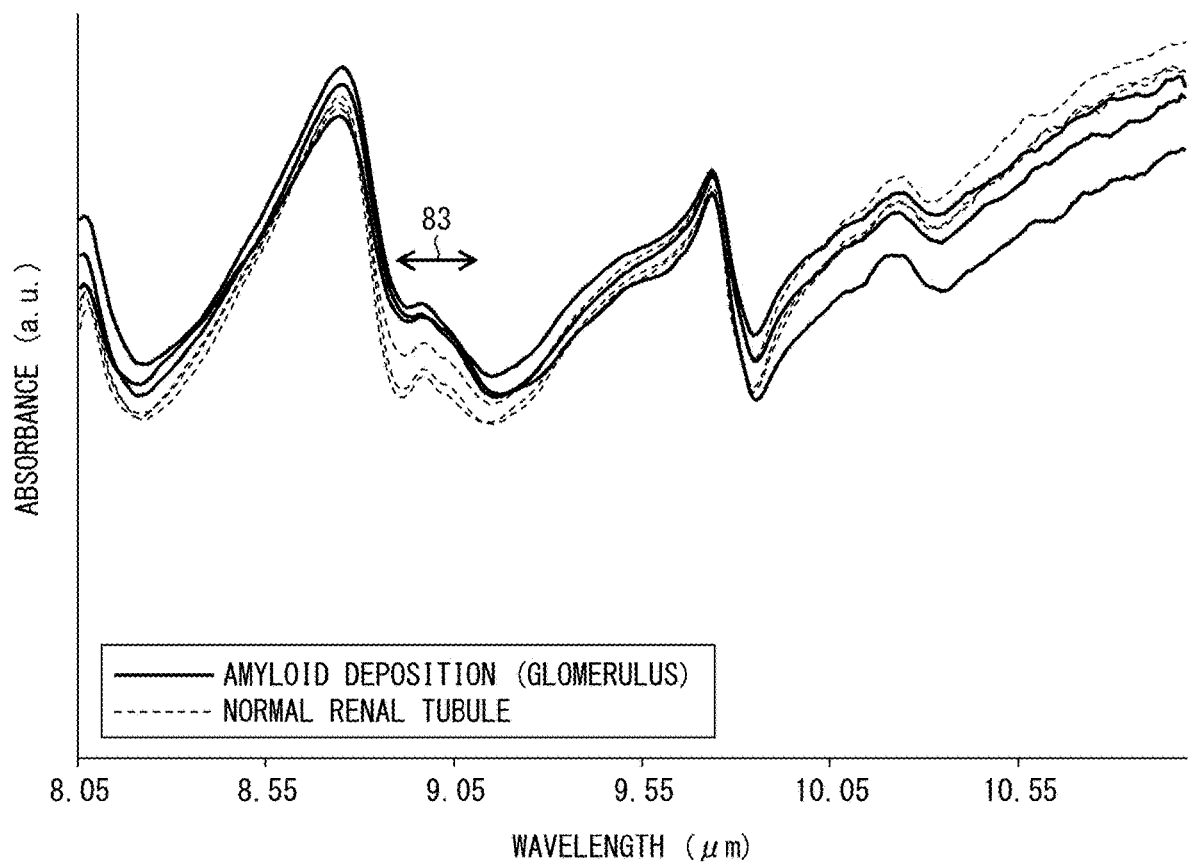

TISSUE IDENTIFICATION DEVICE, TISSUE IDENTIFICATION SYSTEM, METHOD OF IDENTIFYING TISSUE, AND STORAGE MEDIUM

CROSS-REFERENCE TO RELATED APPLICATIONS

This application is a U.S. National Stage Application of International Patent Application No. PCT/JP2019/017863, filed on Apr. 26, 2019, which claims priority to Japanese Patent Application No. 2018-090871, filed on May 9, 2018.

TECHNICAL FIELD

The present invention relates to a device configured to identify biological tissue, a tissue identification system, a method of identifying biological tissue, and an endoscope system.

BACKGROUND ART

There is a known technique to determine the type or state of biological tissue, in particular, whether or not there is a tumor such as a cancer, by means of absorbance analysis. For example, Patent Literatures 1 to 3 each disclose a technique involving: measuring an absorbance spectrum in a broad infrared range including near-infrared light by Fourier Transform Infrared Spectroscopy (FTIR); and determining whether or not there is cancer tissue based on the absorbance spectrum.

The use of such an optical process makes it possible to identify biological tissue noninvasively. Furthermore, by analyzing the obtained absorbance spectrum in accordance with a predetermined algorithm, it is possible to obtain an identification result which is objective and is not based on the subjective view of an inspector.

CITATION LIST

Patent Literature

[Patent Literature 1]
PCT International Publication No. WO2011/151825
[Patent Literature 2]
PCT International Publication No. WO97/18566
[Patent Literature 3]
PCT International Publication No. WO2013/139348

SUMMARY OF INVENTION

Technical Problem

However, according to the techniques using FTIR disclosed in Patent Literatures 1 to 3, an absorbance spectrum in a broad wavelength range is acquired and the shape of the acquired absorbance spectrum in its entirety is analyzed; therefore, the identification requires processing a large amount of information. This increases the time for biological tissue to be identified.

An object of an aspect of the present invention is to achieve, for example, a biological tissue identification device that is capable of obtaining a result of identification of biological tissue without having to process a large amount of information.

Solution to Problem

In order to attain the above object, a tissue identification device in accordance with an embodiment of the present invention includes: a calculating section configured to acquire a first measured value and a second measured value and calculate a ratio of the first measured value to the second measured value or a reciprocal of the ratio; and an identification information generating section configured to generate identification information indicative of a type or a state of biological tissue by determining within which of a plurality of preset numerical ranges the ratio or the reciprocal calculated by the calculating section falls, wherein the first measured value is a transmittance, a reflectance, or an absorbance indicated by a transmitted portion of first inspection light transmitted through the biological tissue or a reflected portion of first inspection light reflected from the biological tissue, the second measured value is a transmittance, a reflectance, or an absorbance indicated by a transmitted portion of second inspection light transmitted through the biological tissue or a reflected portion of second inspection light reflected from the biological tissue, and the first inspection light and the second inspection light have respective different peak wavelengths in a range of from 2 μm to 20 μm, inclusive.

A method of identifying tissue in accordance with an embodiment of the present invention is a method including the steps of: applying, to biological tissue, first inspection light and second inspection light having respective different peak wavelengths in a range of from 2 μm to 20 μm, inclusive; acquiring a first measured value and a second measured value, the first measured value being indicative of a transmittance, a reflectance, or an absorbance indicated by a transmitted portion of the first inspection light transmitted through the biological tissue or a reflected portion of the first inspection light reflected from the biological tissue, the second measured value being indicative of a transmittance, a reflectance, or an absorbance indicated by a transmitted portion of the second inspection light transmitted through the biological tissue or a reflected portion of the second inspection light reflected from the biological tissue; calculating a ratio of the first measured value to the second measured value or a reciprocal of the ratio; and outputting identification information to an output device, the identification information being information that is generated by determining within which of a plurality of preset numerical ranges the ratio or the reciprocal falls and that is indicative of a type or a state of the biological tissue.

An endoscope system in accordance with an embodiment of the present invention includes: a first light source configured to emit inspection light having a peak wavelength in a range of from 2 μm to 20 μm, inclusive; a second light source configured to emit visible light; a first optical fiber configured to guide the inspection light emitted from the first light source; a second optical fiber configured to guide the visible light emitted from the second light source; a first light receiving section configured to receive a transmitted portion of the inspection light transmitted through biological tissue or a reflected portion of the inspection light reflected from the biological tissue; and a second light receiving section configured to receive a transmitted portion of the visible light transmitted through the biological tissue or a reflected portion of the visible light reflected from the biological tissue, the first optical fiber and the second optical fiber being arranged coaxially with each other.

An inspection method in accordance with an embodiment of the present invention includes the steps of: applying, to biological tissue, first inspection light and second inspection light which have respective different peak wavelengths in a range of from 2 μm to 20 μm, inclusive; and receiving, by a light detector, transmitted portions of the first inspection light and the second inspection light transmitted through the biological tissue or reflected portions of the first inspection light and the second inspection light reflected from the biological tissue, wherein the first inspection light and the second inspection light each contain a main pulse and a subpulse, and in the step of receiving, a time for which the light detector is allowed to receive light is limited so that at least part of light resulting from the subpulse is not received.

Advantageous Effects of Invention

An aspect of the present invention makes it possible to obtain a result of identification of biological tissue without having to process a large amount of information.

Figure 8:
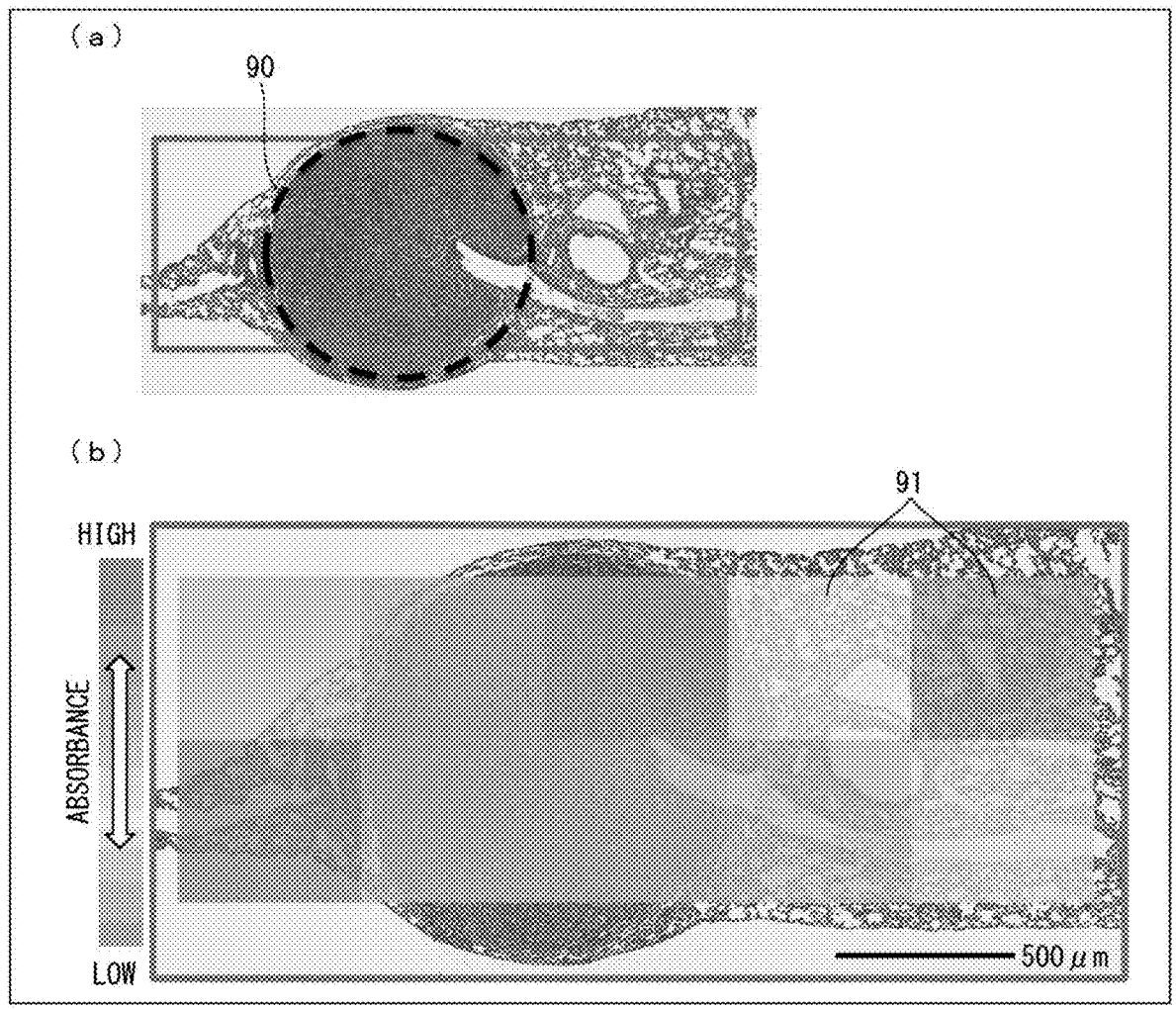

(a) of FIG. 8 shows an example of an image of a sample. (b) of FIG. 8 shows an example of an image in a case where identification information is displayed on a display section.

Figure 9:
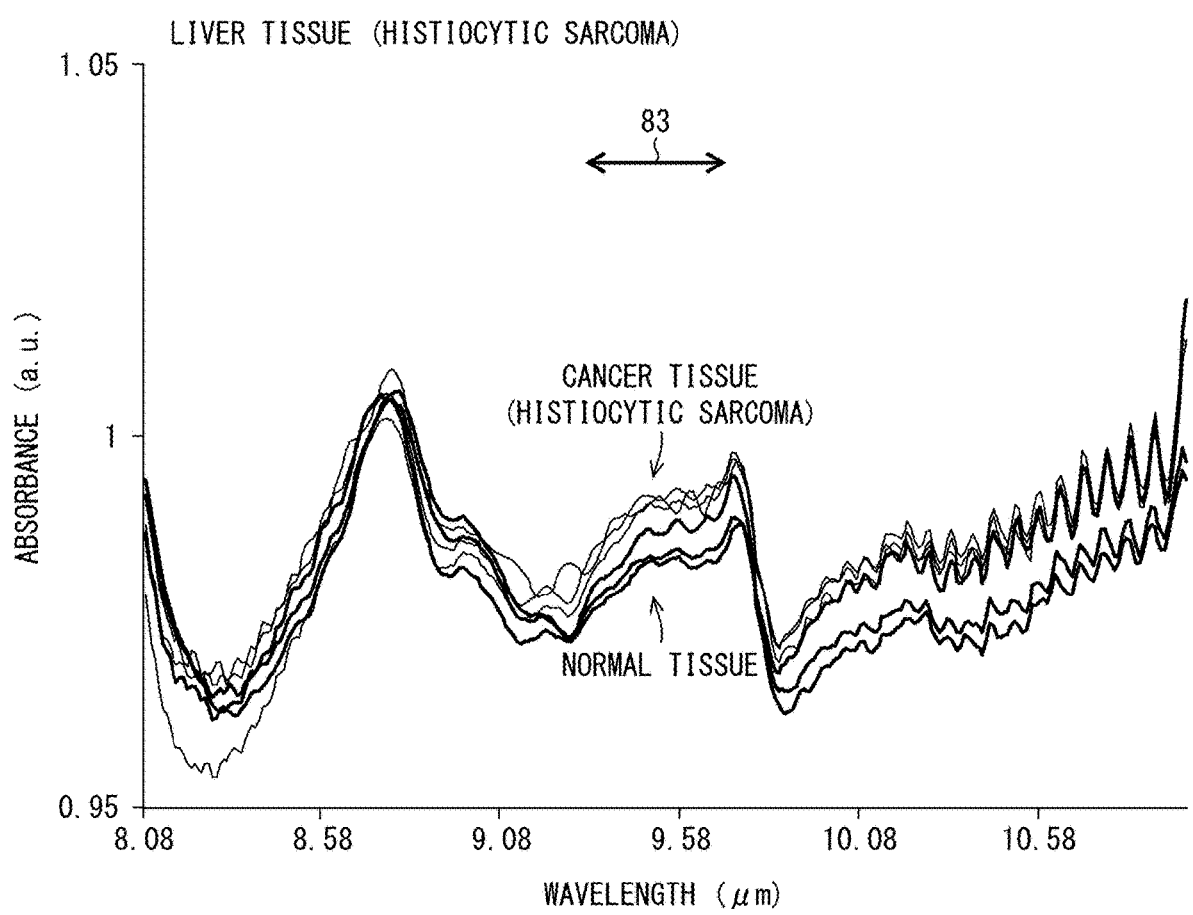

FIG. 9 is a chart showing absorbance spectra of normal tissue and cancer tissue (histiocytic sarcoma) in liver tissue.

Figure 10:
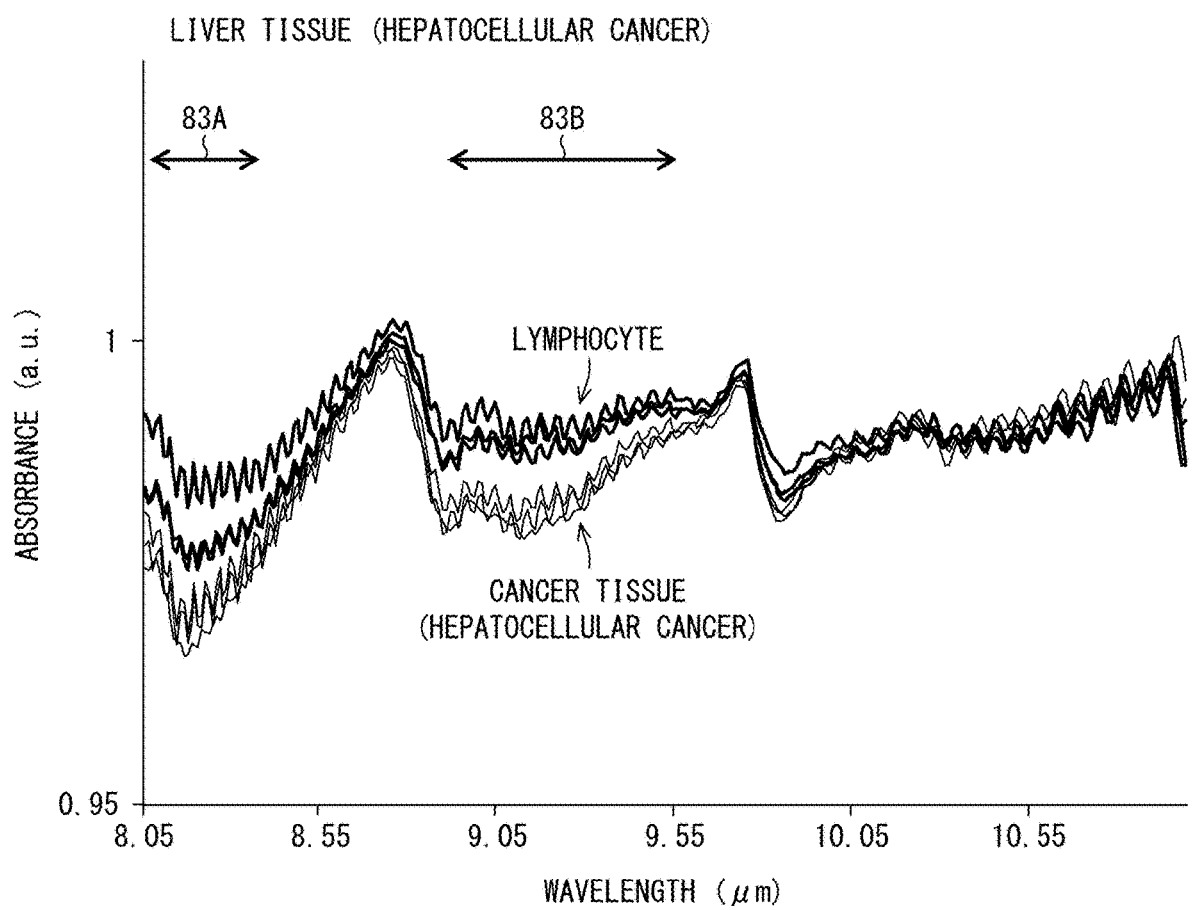

FIG. 10 is a chart showing absorbance spectra of cancer tissue (hepatocellular cancer) and lymphocyte in the liver.

Figure 11:
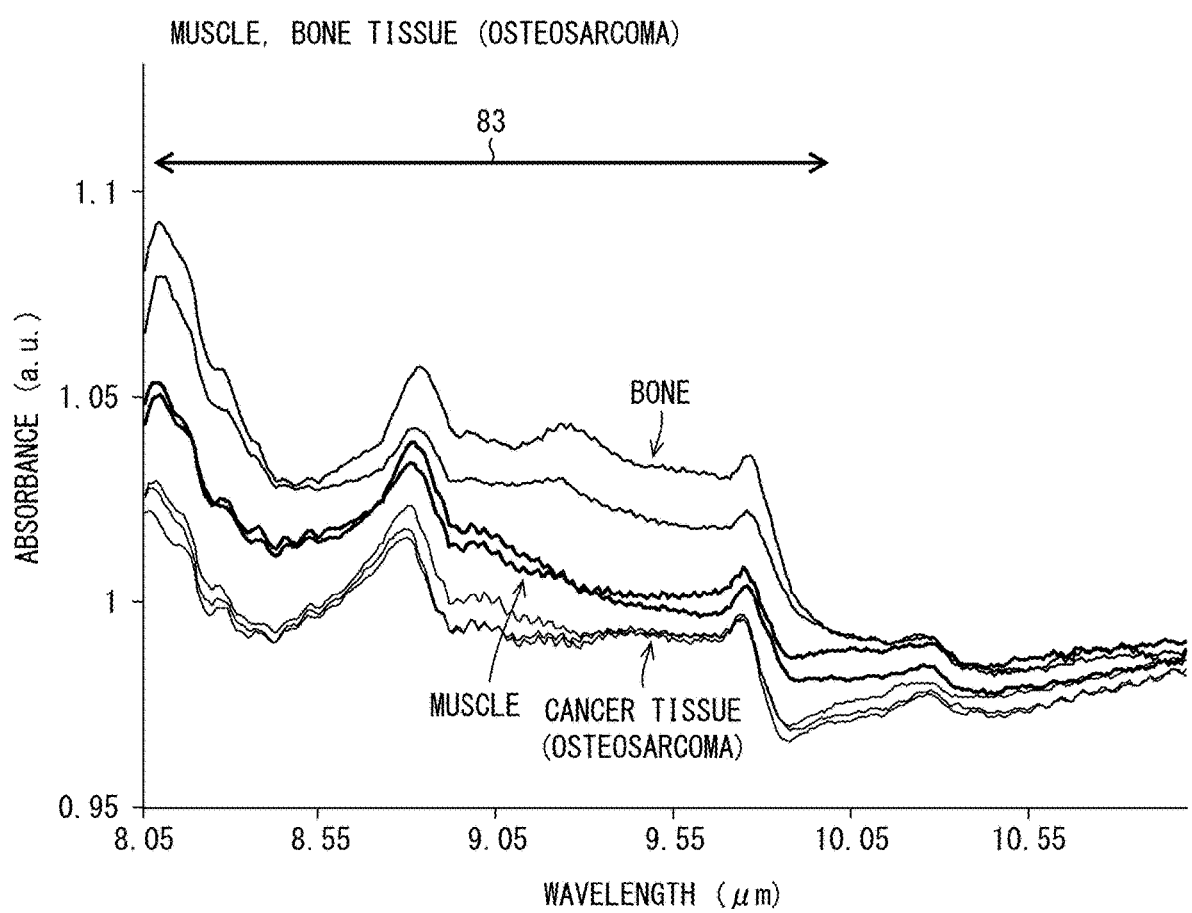

FIG. 11 is a chart showing absorbance spectra of normal tissue of muscle, normal tissue of bone, and cancer tissue (osteosarcoma).

Figure 12:
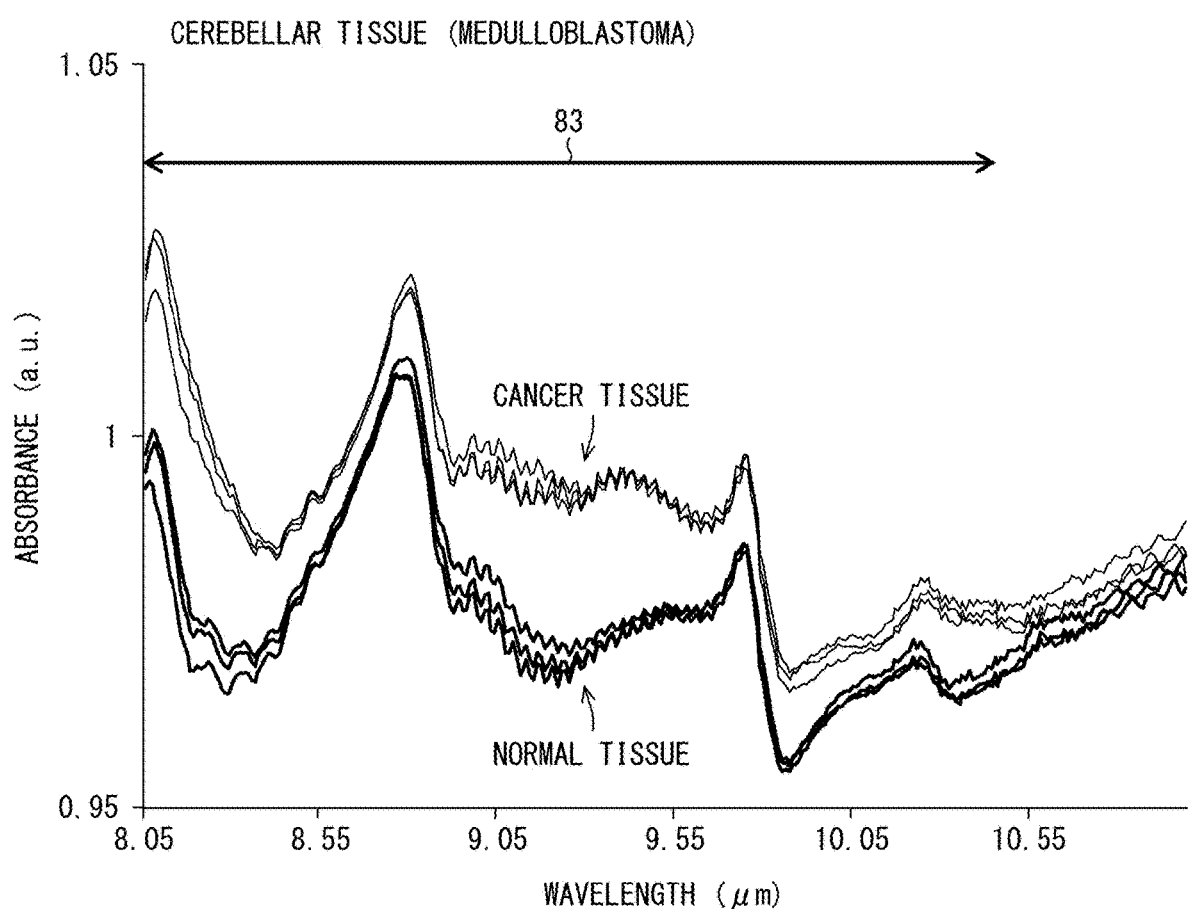

FIG. 12 is a chart showing absorbance spectra of normal tissue and cancer tissue (medulloblastoma) in the cerebellum.

Figure 13:
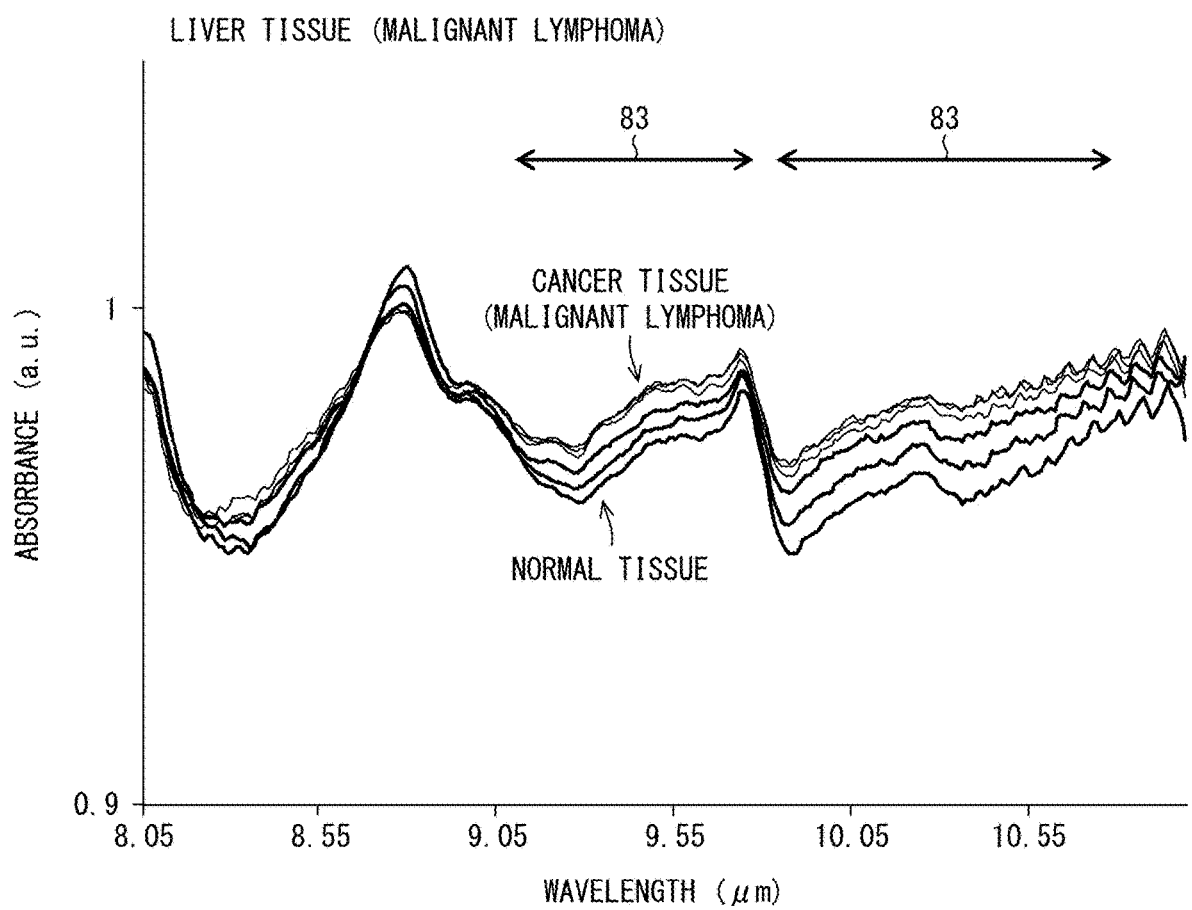

FIG. 13 is a chart showing absorbance spectra of normal tissue and cancer tissue (malignant lymphoma) in the liver.

Figure 14:
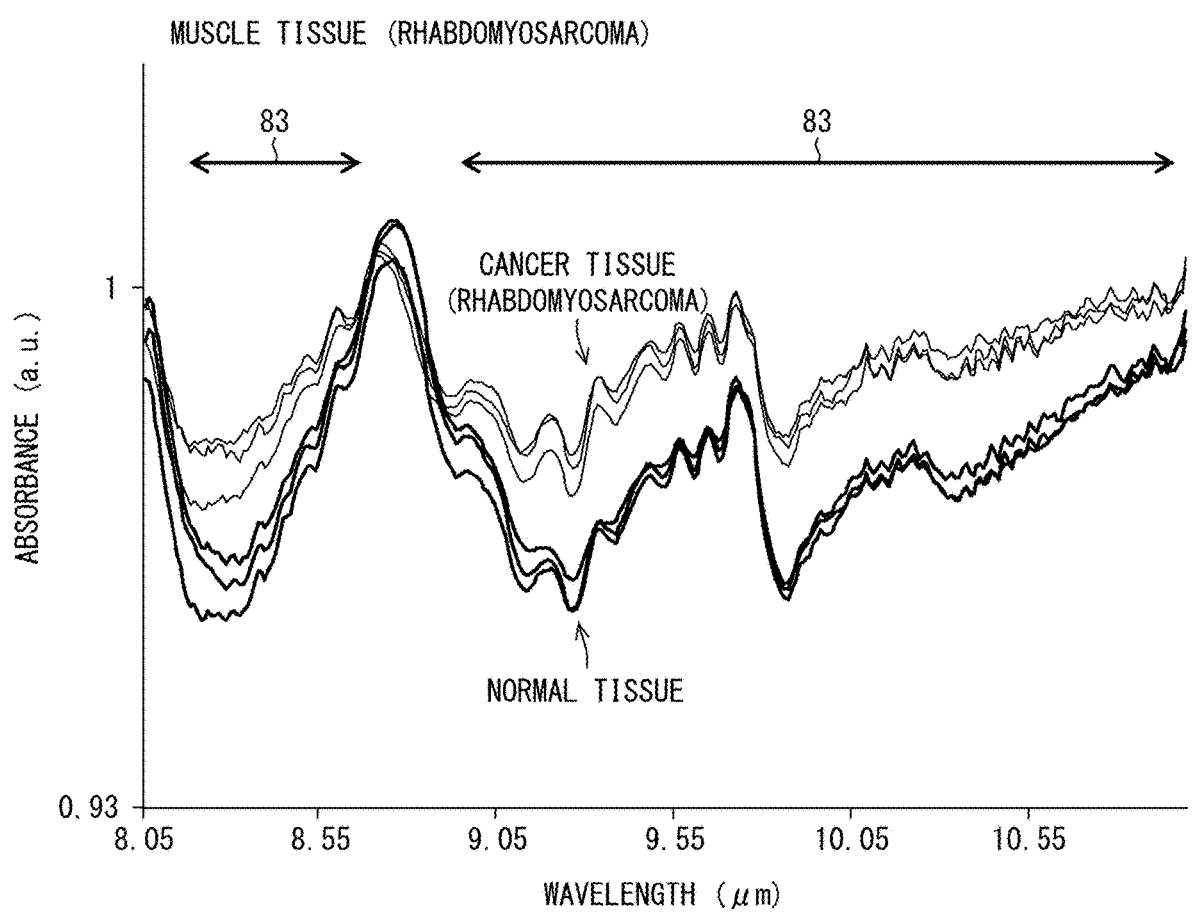

FIG. 14 is a chart showing absorbance spectra of normal tissue and cancer tissue (rhabdomyosarcoma) of muscle.

Figure 15:
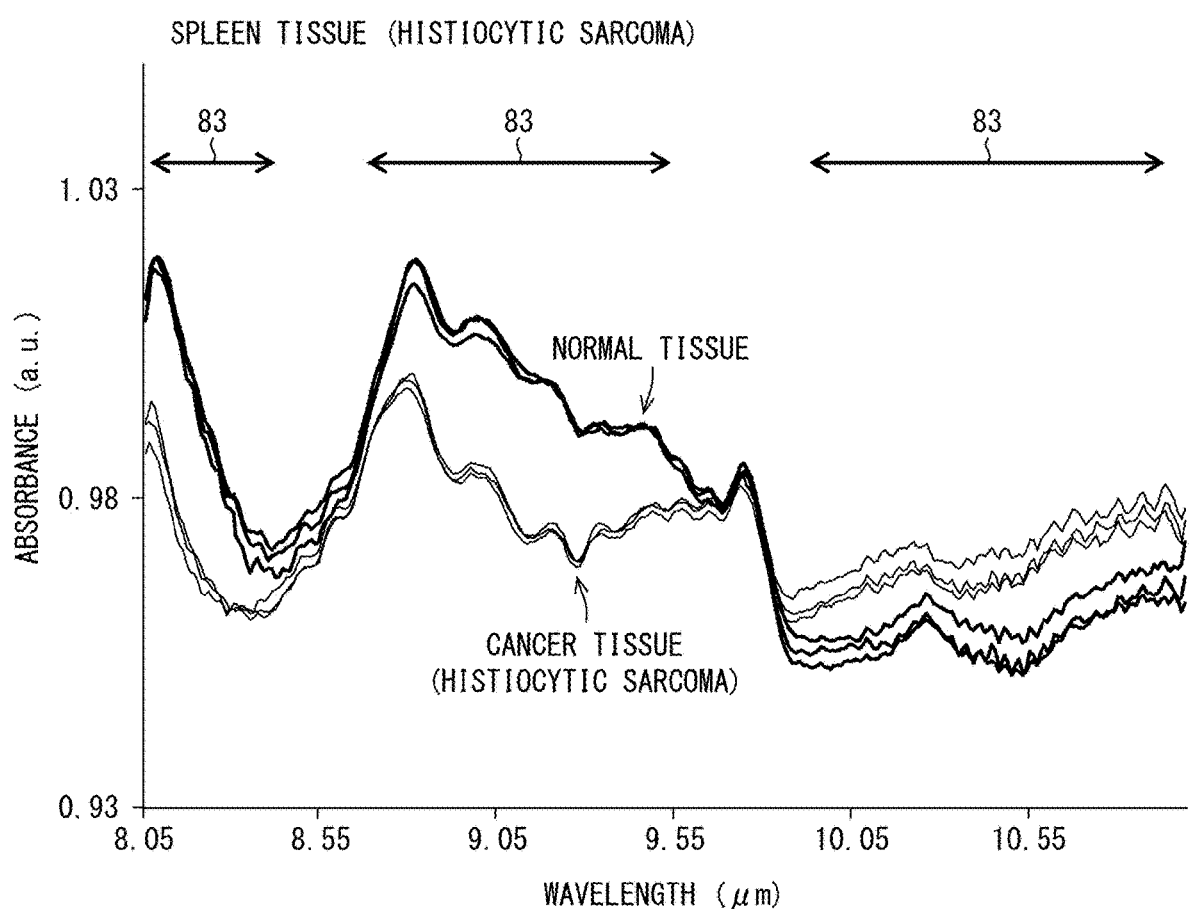

FIG. 15 is a chart showing absorbance spectra of normal tissue and cancer tissue (histiocytic sarcoma) in the spleen.

Figure 16:
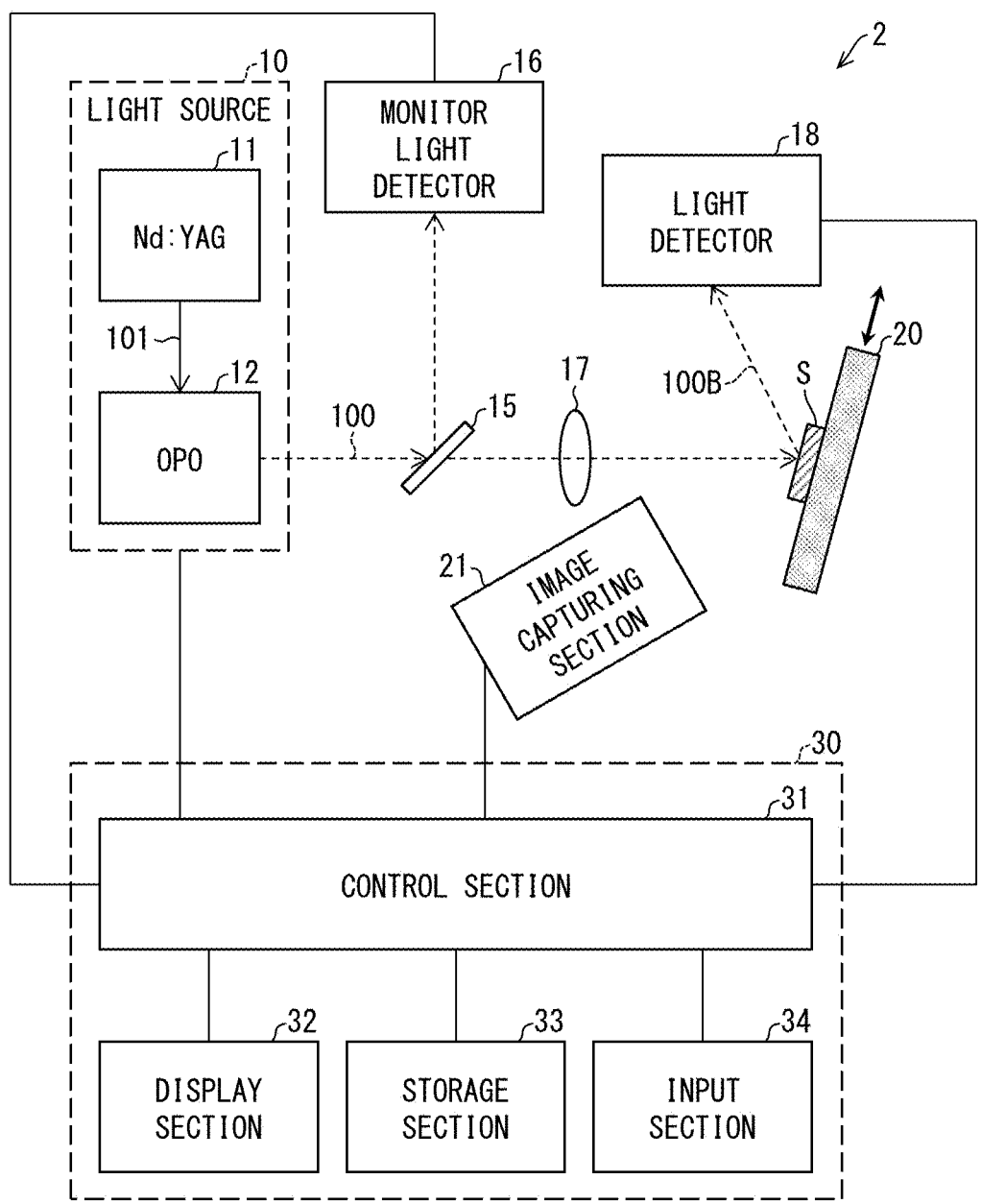

FIG. 16 illustrates a configuration of a biological tissue identification system in accordance with Embodiment 2.

Figure 17:
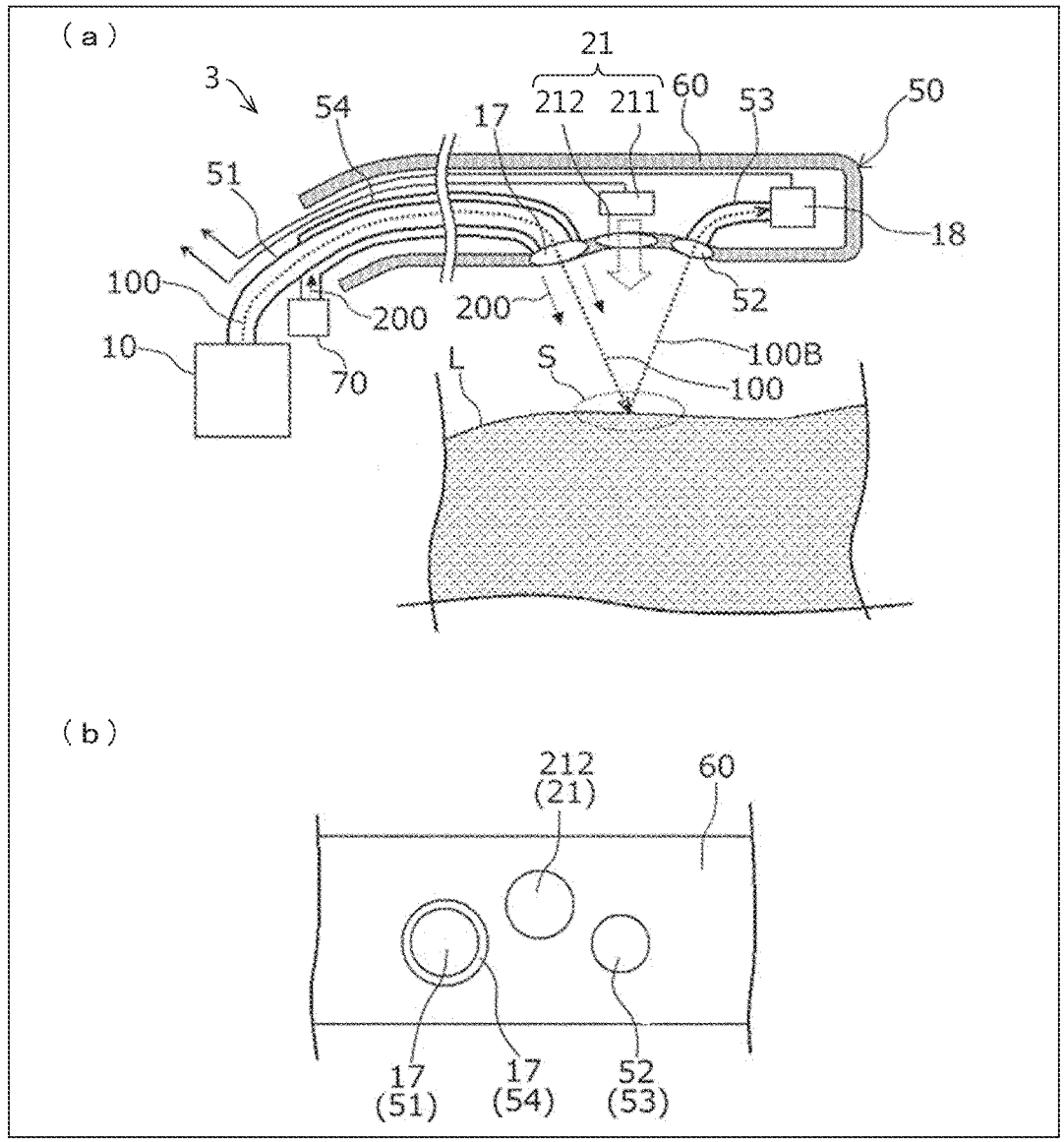

(a) of FIG. 17 is a cross-sectional view illustrating a configuration of an endoscope system. (b) of FIG. 17 illustrates a side wall of a tube.

Figure 18:
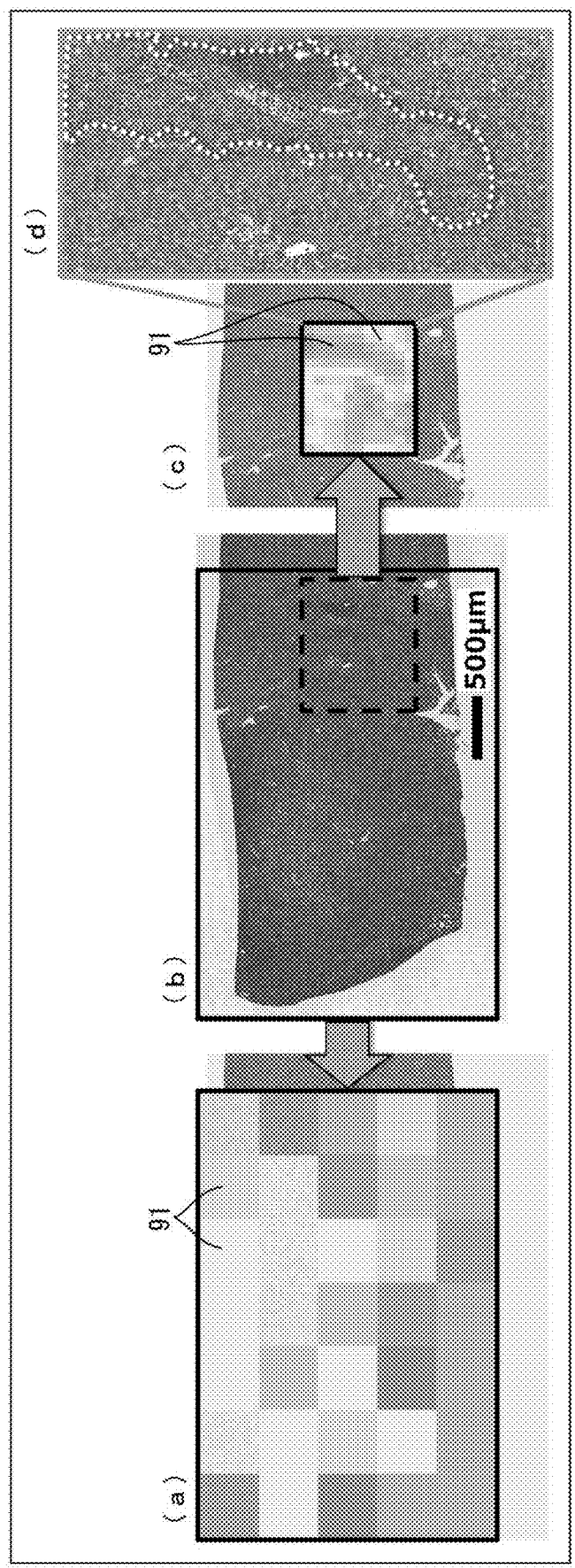

(a) of FIG. 18 shows an image displayed on a display section as identification information for biological tissue. (b) of FIG. 18 is an image of liver tissue which is to be identified. (c) of FIG. 18 is the image of the liver tissue on which another image (i.e., identification information) is superimposed. (d) of FIG. 18 is an enlarged view of a part of the image of the liver tissue enclosed by solid line in (c) of FIG. 18.

Figure 19:
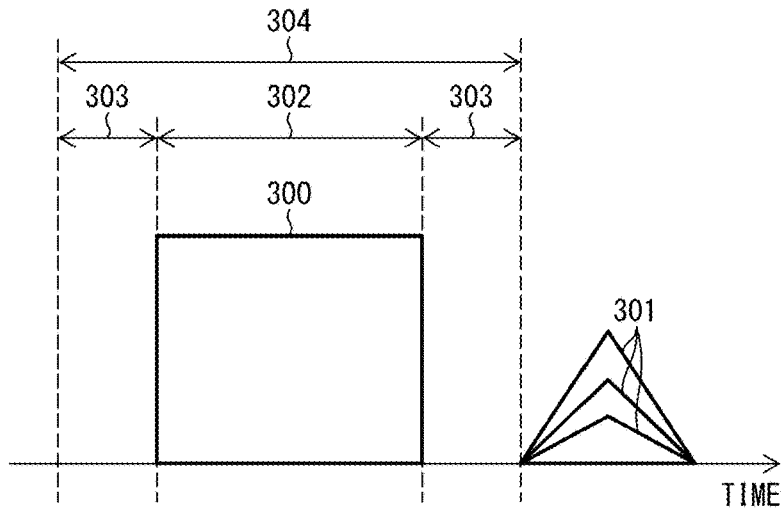

FIG. 19 illustrates the waveforms of pulses obtained during oscillation of laser light.

Figure 20:
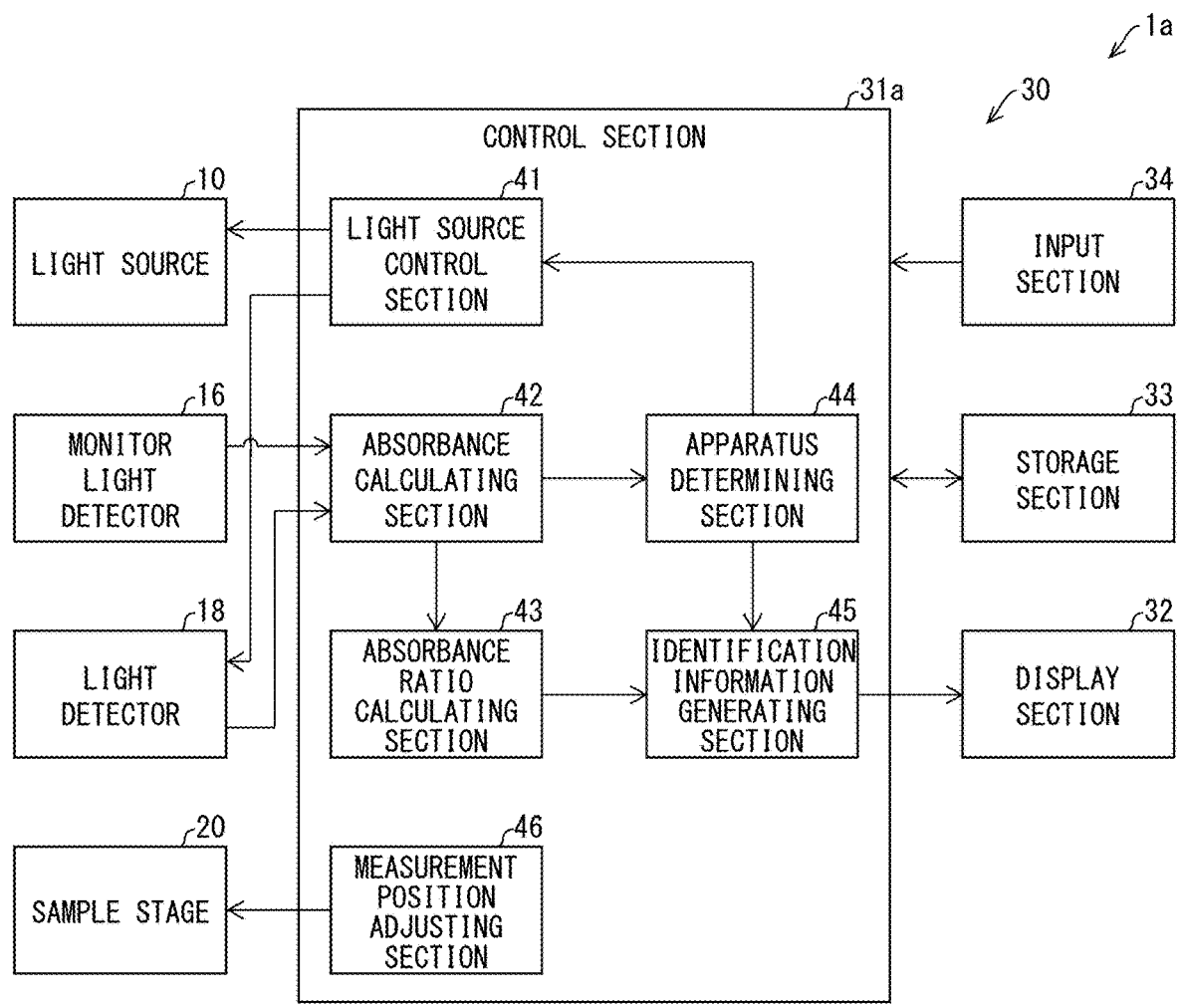

FIG. 20 is a functional block diagram illustrating a configuration of a control section of a biological tissue identification system in accordance with Embodiment 4.

FIG. 21 shows charts showing absorbance spectra of normal liver and an area infiltrated with malignant lymphoma cells in liver tissue. (a) of FIG. 21 shows absorbance spectra obtained with use of the biological tissue identification system in accordance with Embodiment 1, and (b) of FIG. 21 shows absorbance spectra obtained with use of the biological tissue identification system in accordance with Embodiment 4.

Figure 22:
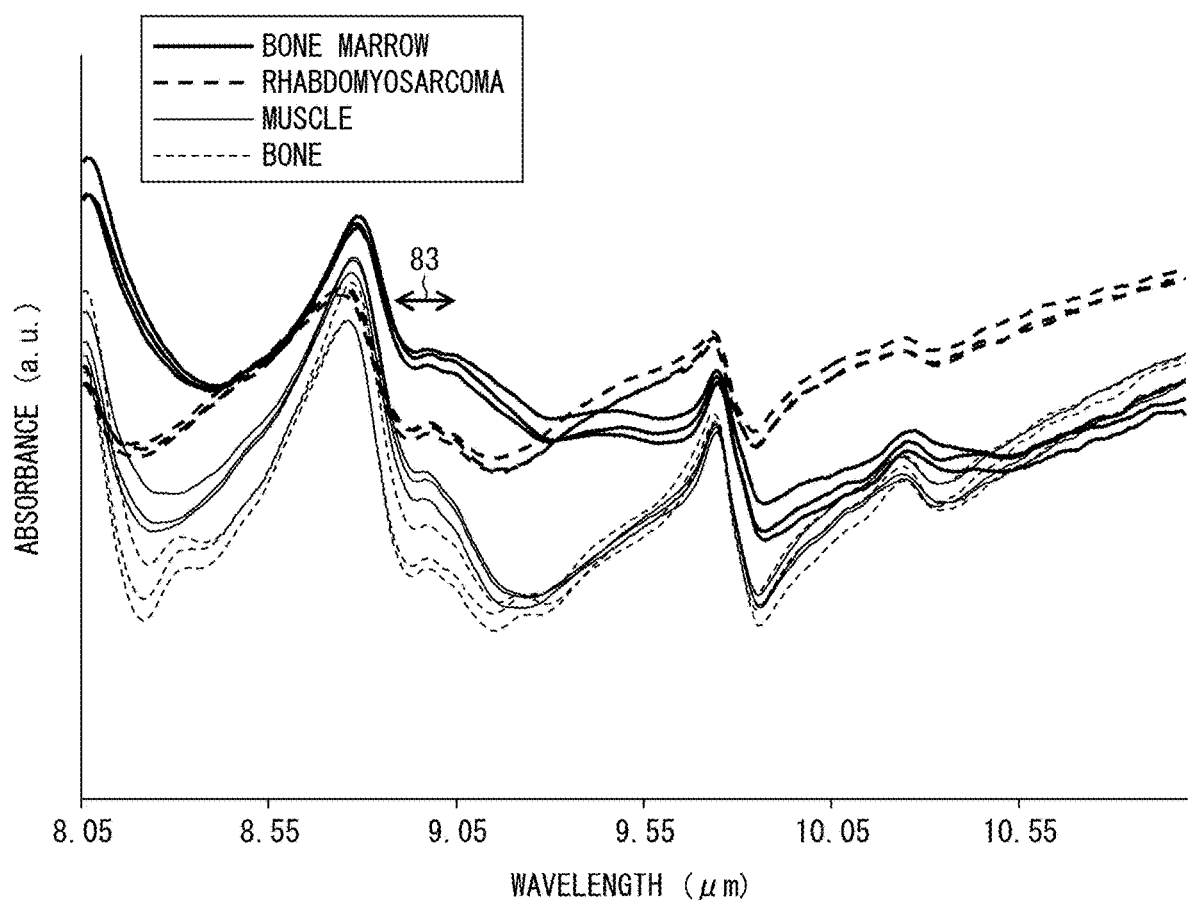

FIG. 22 is a chart showing absorbance spectra of a plurality of different types of normal tissue and cancer tissue.

Figure 23:
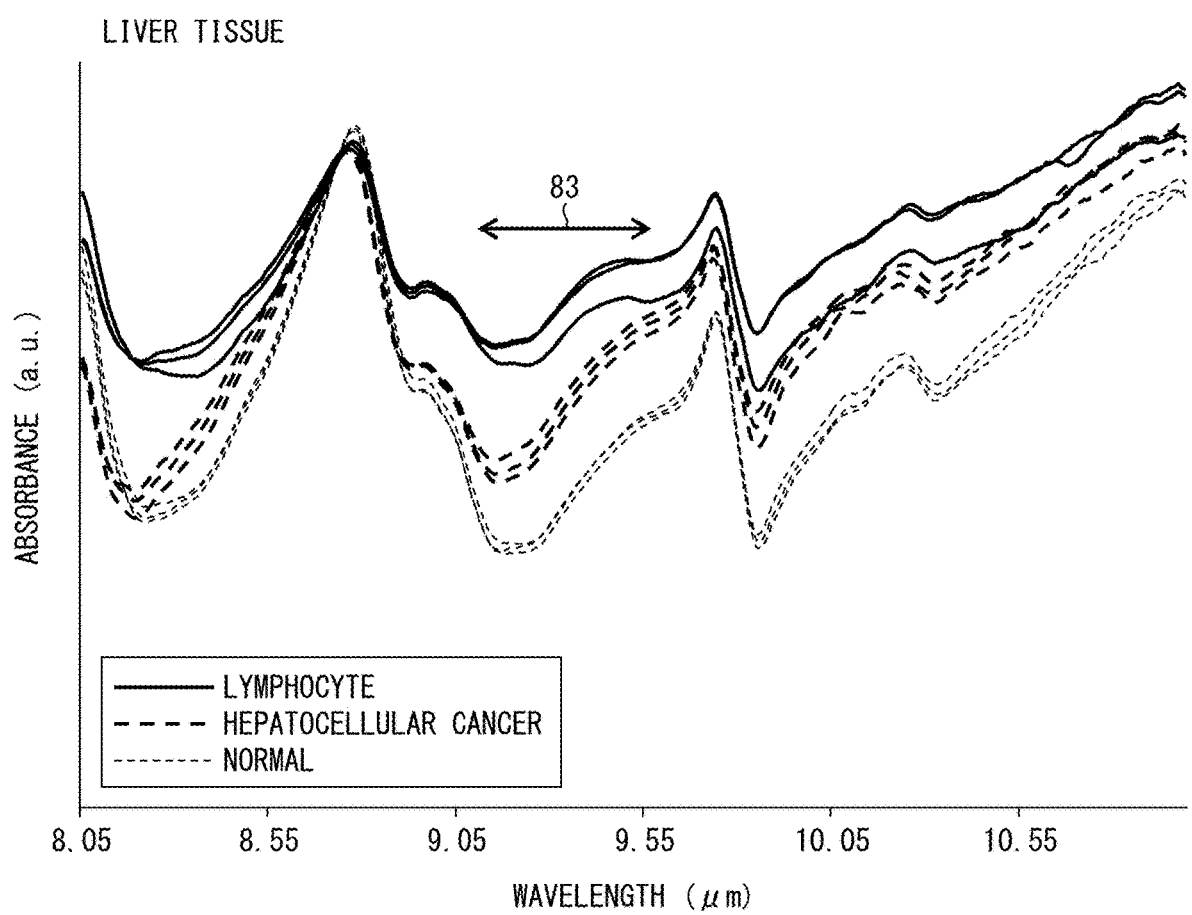

FIG. 23 is a chart showing absorbance spectra of normal tissue, cancer tissue, and lymphocyte in liver tissue.

Figure 24:
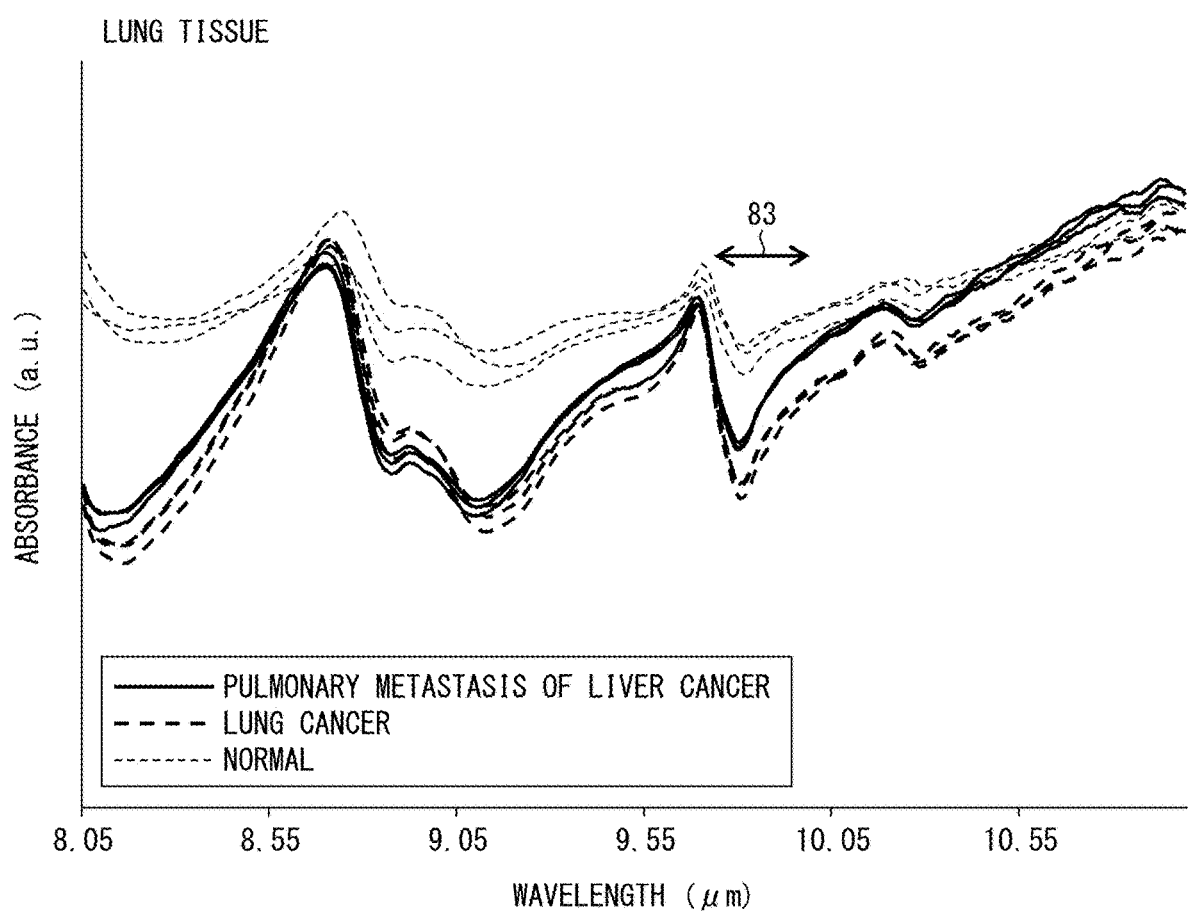

FIG. 24 is a chart showing absorbance spectra of normal tissue, primary lung cancer tissue, and a lesion of pulmonary metastasis of liver cancer in lung tissue.

Figure 25:
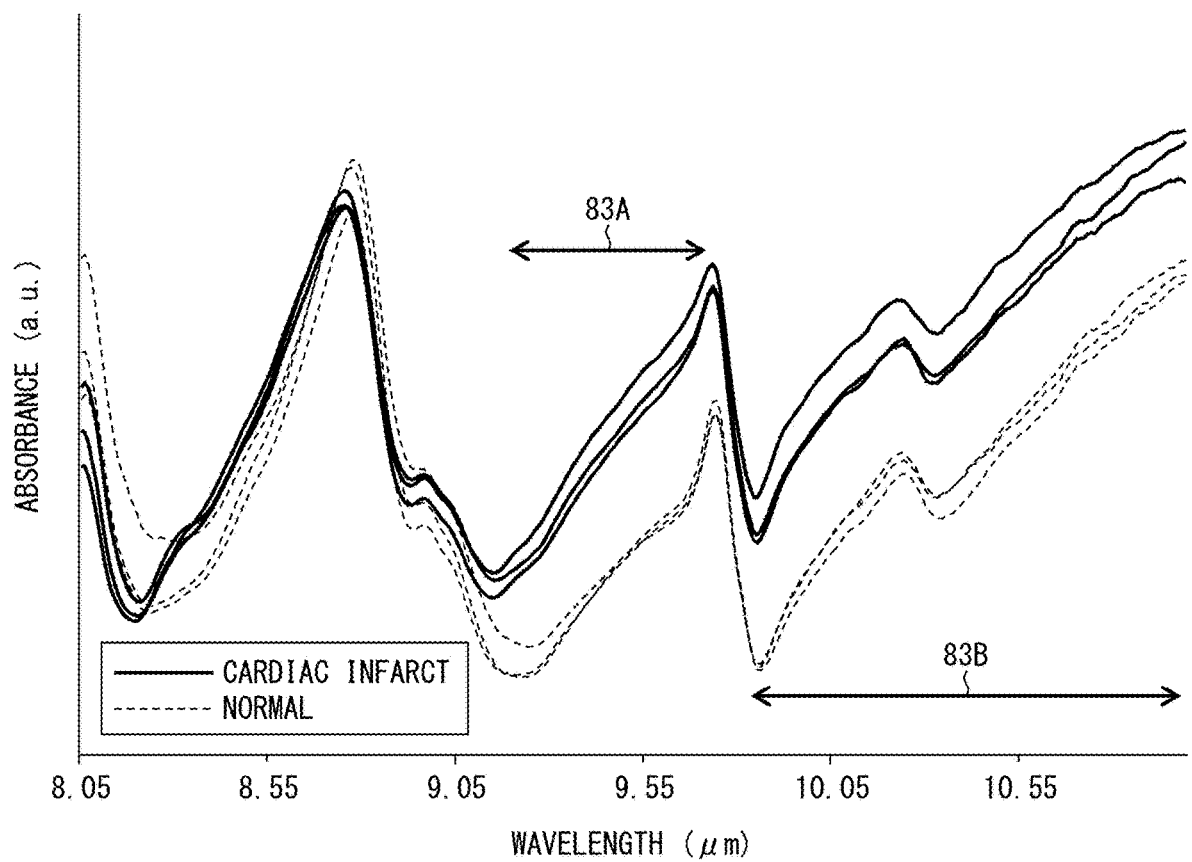

FIG. 25 is a chart showing absorbance spectra of normal tissue and a cardiac infarct area in heart tissue.

Figure 26:
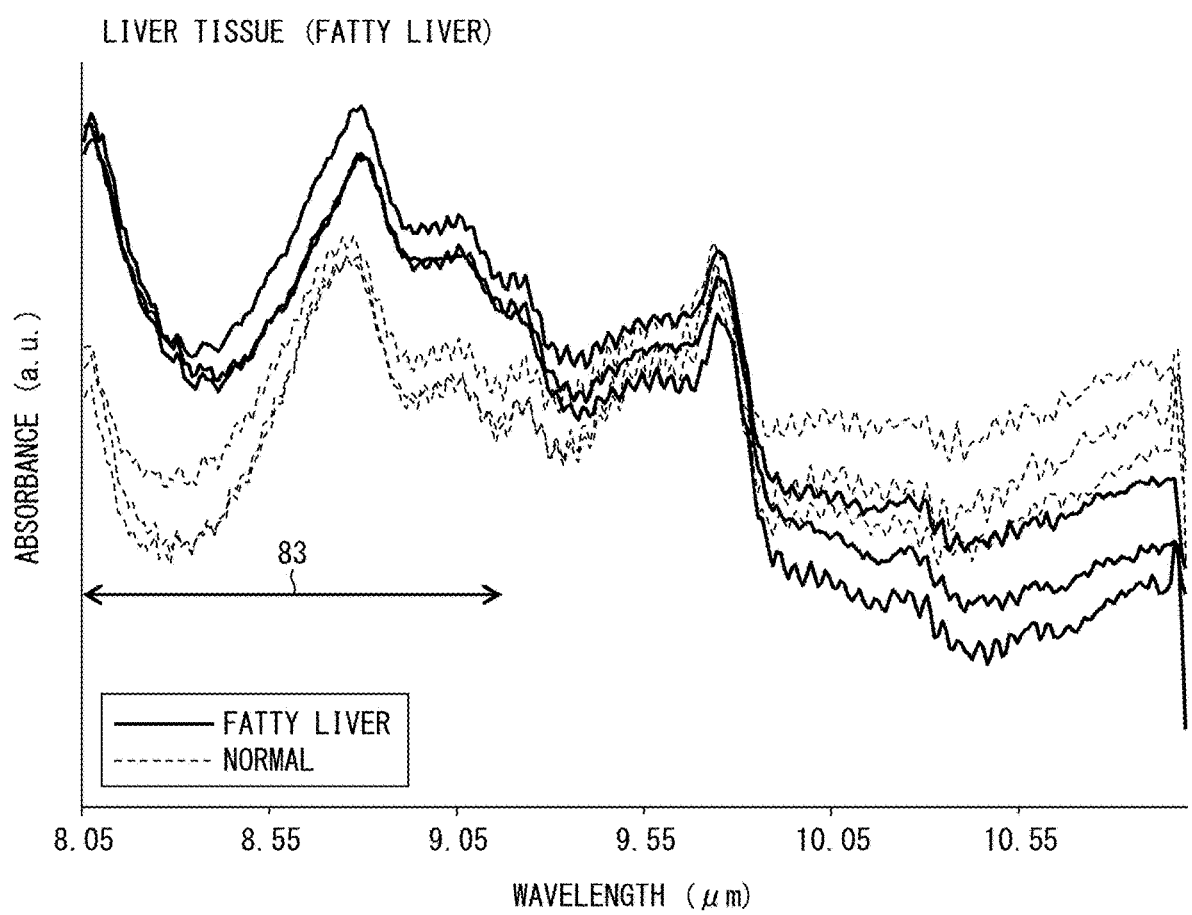

FIG. 26 is a chart showing absorbance spectra of normal tissue and tissue of fatty liver in liver tissue.

Figure 27:
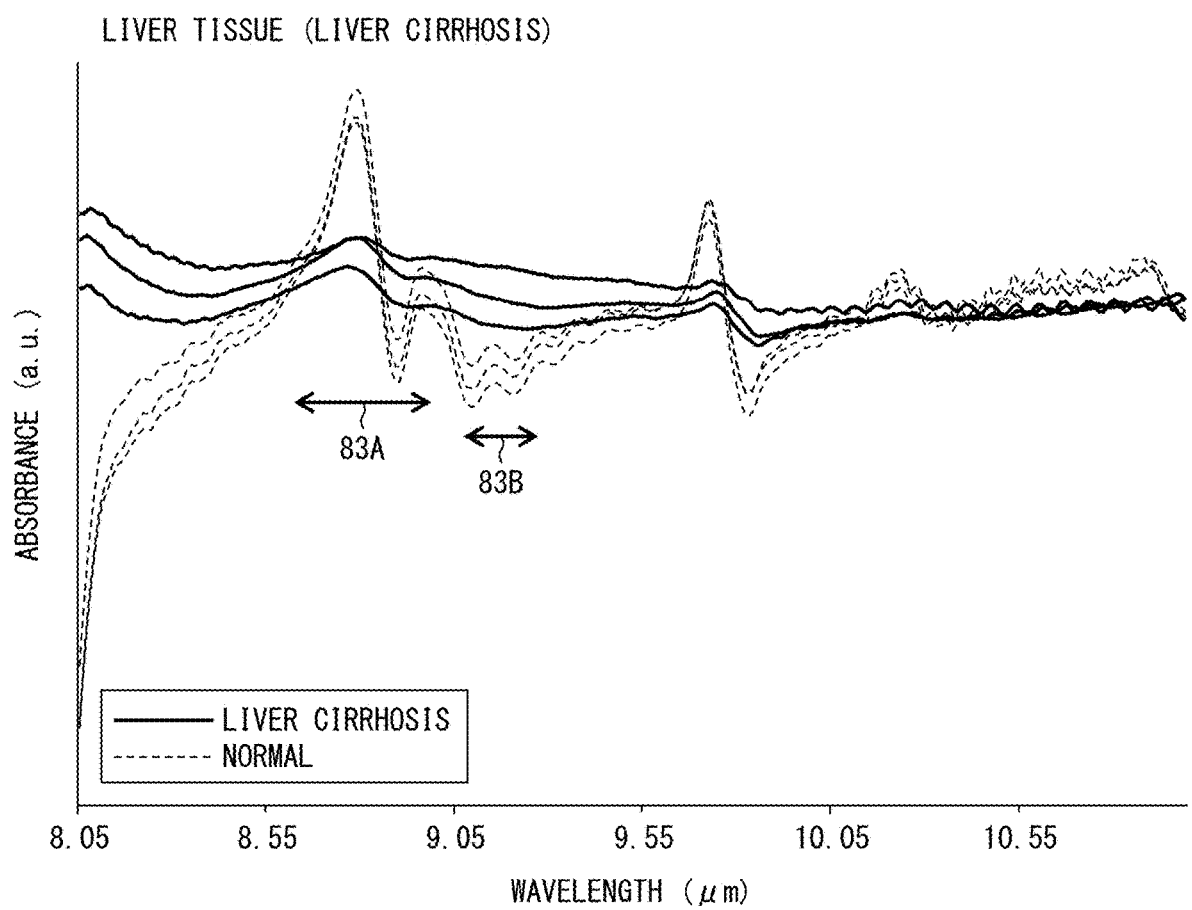

FIG. 27 is a chart showing absorbance spectra of normal tissue and tissue of liver cirrhosis in liver tissue.

FIG. 28 is a chart showing absorbance spectra of normal tissue, radiation-induced cancer tissue, and spontaneous cancer tissue in cerebellar tissue.

FIG. 29 is a chart showing absorbance spectra of a normal renal tubule and a glomerulus with amyloid deposition in kidney tissue.

DESCRIPTION OF EMBODIMENTS

Embodiment 1

The following description will discuss an embodiment of the present invention in detail. First, a technical idea of the present invention is discussed. The inventors of the present invention have analyzed absorbance spectra obtained as a result of applying light of various wavelengths to biological tissue. As a result, the inventors of the present invention have found that, by applying, to biological tissue, mid-infrared rays of at least two wavelengths having respective different peak wavelengths in the range of from 2 μm to 20 μm, inclusive and calculating the ratio between the resulting absorbances, it is possible to identify the biological tissue.

Figure 1:
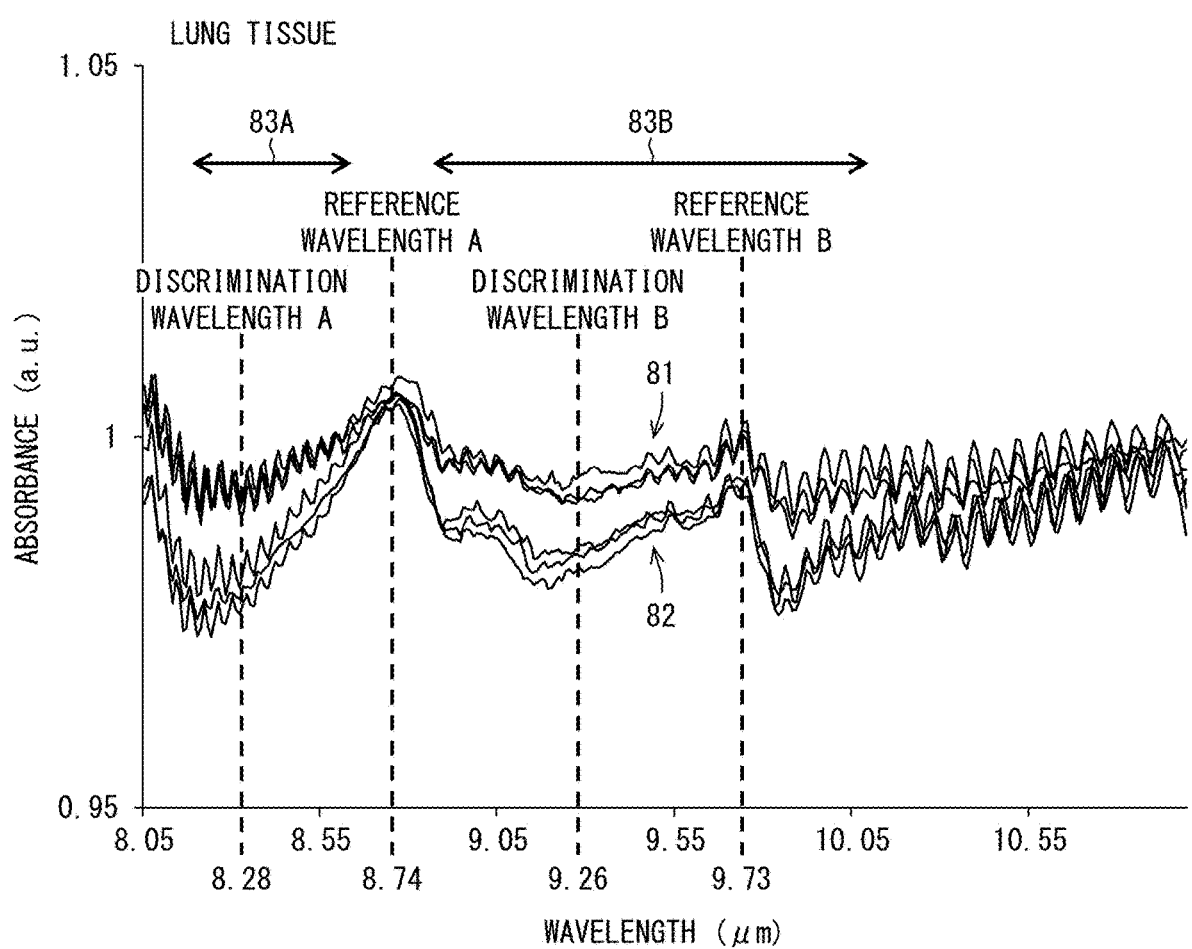
FIG. 1 is a chart showing an example of absorbance spectra obtained by applying mid-infrared rays to lung tissue.

FIG. 1 is a chart showing an example of absorbance spectra obtained by applying mid-infrared rays to lung tissue. Of the absorbance spectra shown in FIG. 1, the absorbance spectra indicated by sign 81 are absorbance spectra of normal tissue, and the absorbance spectra indicated by sign 82 are absorbance spectra of cancer tissue. Note that the absorbance spectrum measurement was carried out a plurality of times on each tissue. Also with regard to the absorbance spectra discussed in the following descriptions, the measurement was carried out a plurality of times on each tissue. As a result of the analysis of such two types of absorbance spectra, the inventors of the present invention have made the following findings.

There is a wavelength range in which the absorbance is unlikely to change irrespective of the type or state of biological tissue (such a wavelength is referred to as "reference wavelength"). This reference wavelength range is a narrow range equivalent to a peak in an absorbance spectrum. In the case of the example shown in FIG. 1, an accurate evaluation can be made by employing a wavelength which is "equivalent to a peak" as the reference wavelength. On the contrary, for example, in the case of the example shown in FIG. 12 (cerebellar tissue), the absorbance at each wavelength which is "equivalent to a peak" differs greatly between normal tissue and cancer tissue, which makes it difficult to make an accurate evaluation. In such a case, an accurate evaluation can be made by using, as the absorbance at a reference wavelength, the average of the absorbances at reference wavelengths of respective types of tissue. Note, however, that the wavelength set as the reference wavelength may be a wavelength corresponding to a dip in an absorbance spectrum or may be a wavelength corresponding to a flat portion of an absorbance spectrum, provided that the wavelength is one at which the absorbance is unlikely to change irrespective of the type or state of biological tissue.

There is a wavelength range in which the absorbance is likely to change depending on the type or state of biological tissue (such a wavelength is referred to as "discrimination wavelength"). In the example shown in FIG. 1, the range represented by arrow 83A (8.06 µm to 8.70 µm) and the range represented by arrow 83B (8.75 µm to 10.05 µm) are the discrimination wavelength ranges.

Light of a reference wavelength (referred to as "reference inspection light" (second inspection light)) is applied to biological tissue, and the absorbance indicated by a transmitted portion of the reference inspection light transmitted through the biological tissue or a reflected portion of the reference inspection light reflected from the biological tissue is used as a reference absorbance (second measured value). Light of a discrimination wavelength (referred to as "discrimination inspection light" (first inspection light)) is applied to biological tissue, and the absorbance indicated by a transmitted portion of the discrimination inspection light transmitted through the biological tissue or a reflected portion of the discrimination inspection light reflected from the biological tissue is used as a discrimination absorbance (first measured value). The ratio of the discrimination absorbance to the reference absorbance (i.e., discrimination absorbance/reference absorbance) or the reciprocal of the ratio (reference absorbance/discrimination absorbance) differs depending on the type or state of biological tissue.

The following is an explanation from a different point of view. The discrimination absorbance obtained by applying discrimination inspection light to biological tissue differs depending on the type or state of the biological tissue (irradiation target) to a greater extent than the reference absorbance obtained by applying reference inspection light to the biological tissue.

By presetting the range of values that the ratio of discrimination absorbance to reference absorbance (this ratio is referred to as "absorbance ratio") (or the reciprocal of the absorbance ratio) can take for each type of biological tissue or for each state of biological tissue, it is possible to identify the type or state of to-be-inspected biological tissue by determining within which of the plurality of the preset numerical ranges the measured absorbance ratio (or the reciprocal of the absorbance ratio) falls.

A reason why the absorbance ratio is used instead of the absolute value of the discrimination absorbance is to increase identification accuracy. In a case where laser light is applied to biological tissue and absorbance is measured, the measured absorbance varies also depending on, for example, the angle of incidence of light, conditions in which light is applied, the thickness of sample S, and the like. Therefore, in order to appropriately discern differences in the absorbance spectrum in the discrimination wavelength range, it is preferable to use the ratio of the discrimination absorbance to the reference absorbance which is measured under the identical irradiation conditions, instead of the absolute value of the discrimination absorbance.

Note that the following description will discuss embodiments in which the ratio of discrimination absorbance to reference absorbance is used as-is instead of using the reciprocal of the ratio. In a case where the reciprocal (reference absorbance/discrimination absorbance) of the ratio is used, it is only necessary that the foregoing plurality of numerical ranges be set so as to correspond to the ranges of values that the reciprocals can take.

FIG. 1 shows a reference wavelength A (8.74 µm), a reference wavelength B (9.73 µm), a discrimination wavelength A (8.28 µm), and a discrimination wavelength B (9.26 µm). In order to identify biological tissue, it is only necessary to use (i) an absorbance (reference absorbance) at at least one reference wavelength and (ii) an absorbance (discrimination absorbance) at at least one discrimination wavelength included in a wavelength range adjacent to the reference wavelength.

For example, the ratio of the absorbance at the discrimination wavelength A to the absorbance at the reference wavelength A (this ratio is absorbance ratio) is calculated for the absorbance spectrum of normal tissue and for the absorbance spectrum of cancer tissue. In the case of the example shown in FIG. 1, the absorbance ratio for the normal tissue is greater than the absorbance ratio for the cancer tissue. Therefore, by finding and setting in advance the range of values that each of these absorbance ratios can take, it is possible to determine whether to-be-inspected biological tissue contains cancer tissue or not by determining whether the measured absorbance ratio is included in the range of values that normal tissue can take or in the range of values that the cancer tissue can take. Note that there are also cases in which the absorbance ratio for normal tissue is smaller than the absorbance ratio for cancer tissue.

In the example shown in FIG. 1, in a case where the reference wavelength A and the discrimination wavelength A are used and in a case where the reference wavelength A and the discrimination wavelength B are used, the value at the border between the range of values that the normal tissue can take and the range of values that the cancer tissue can take (such a value is "threshold") can be set to 0.986. In this instance, in a case where the absorbance ratio is smaller than 0.986, the biological tissue can be determined as cancer tissue.

According to conventional techniques, whether biological tissue contains cancer tissue or not is determined by comparing the waveform of the absorbance spectrum of the biological tissue with waveforms stored in a database. In contrast, according to the present invention, the identification of biological tissue is carried out by: applying mid-infrared rays of at least two wavelengths having respective peak wavelengths in the range of from 2 µm to 20 µm, inclusive; and identifying the biological tissue based on the ratio between the resulting absorbances. This eliminates the need for the acquisition of absorbance spectra over a broad wavelength range, and makes it possible to shorten the time for absorbance measurement. Furthermore, since the biological tissue can be identified based on the absorbance ratio, only a small amount of information needs to be processed to carry out identification. This makes it possible to shorten operation time. Furthermore, since biological tissue is identified based on the absorbance ratio, it is possible to carry out objective identification which is not based on the subjective view of an inspector. The number of preset ranges of values that the absorbance ratios can take may be two or three or more. For example, numerical ranges for three or more stages may be set corresponding to the degrees of malignancy of cancer.

The findings described so far apply also to (1) the relationship between the transmittance of reference inspection light transmitted through biological tissue and the transmittance of discrimination inspection light transmitted through the biological tissue and (2) the relationship between the reflectance of reference inspection light reflected from biological tissue and the reflectance of discrimination inspection light reflected from the biological tissue. This is because absorbance, transmittance, and reflectance can be converted into one another. In Embodiment 1, examples in which absorbance is used are only mentioned.

(Configuration of Biological Tissue Identification System 1)

Figure 2:
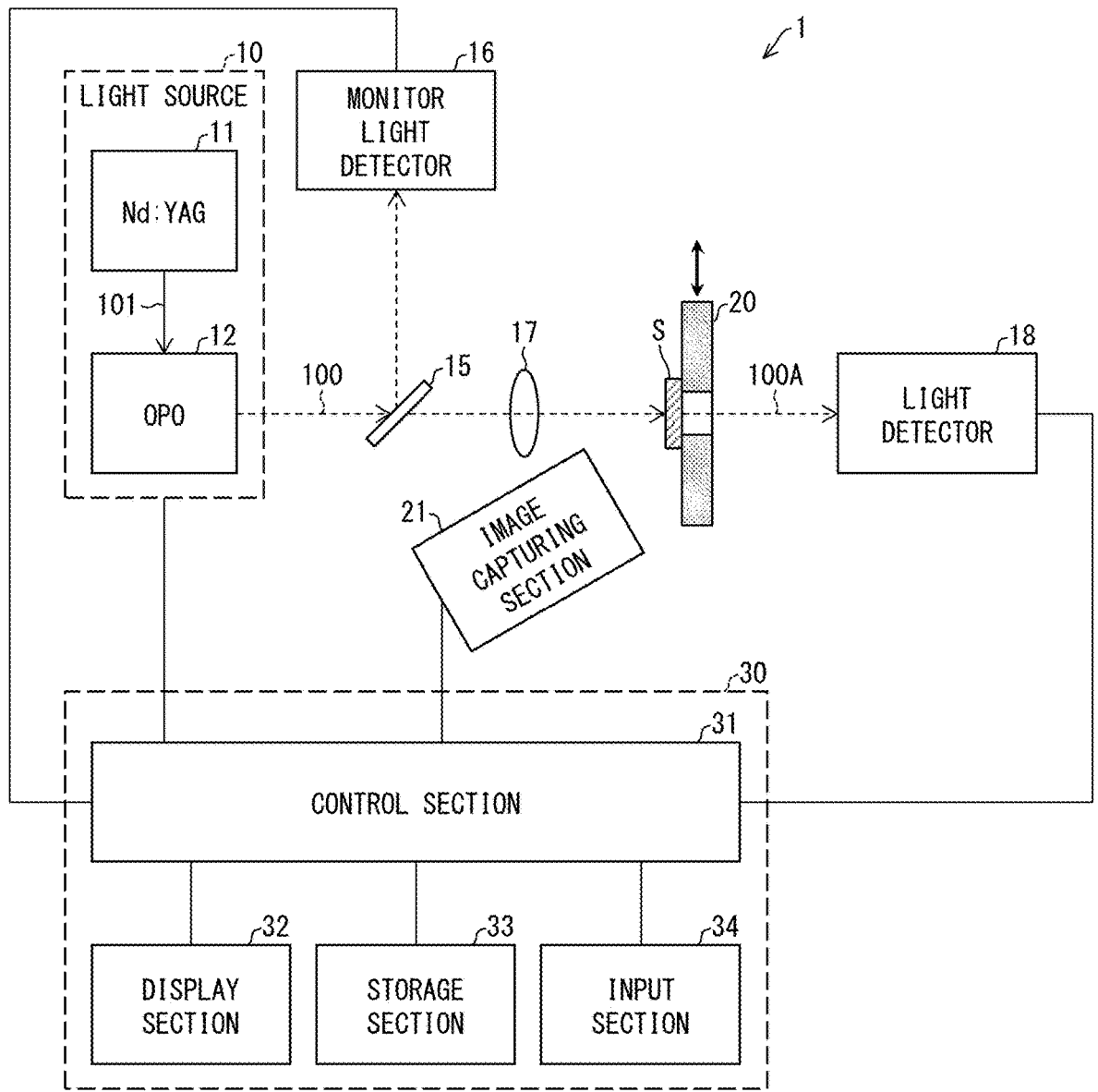
FIG. 2 illustrates a configuration of a biological tissue identification system in accordance with Embodiment 1.

FIG. 2 illustrates a configuration of a biological tissue identification system 1 in accordance with Embodiment 1. The biological tissue identification system 1 identifies biological tissue contained in a sample S by: applying mid-infrared light to the sample S on a sample stage 20; and measuring the absorbance of light transmitted through the sample S. The biological tissue contained in the sample S may be tissue taken from a human or may be tissue taken from a non-human animal such as a mouse or a rat.

A light source 10 for use in the biological tissue identification system 1 is a laser light source that selectively oscillates mid-infrared light having a specific peak wavelength in the range of from 2 μm to 20 μm (i.e., a light source capable of switching wavelengths). In order to increase the accuracy and efficiency of absorbance measurement, it is preferable to use, as the light source 10, a light source including a quantum cascade laser that oscillates high-intensity mid-infrared laser light or a light source including an optical parametric oscillator (OPO).

Since laser light is used as inspection light, it is possible to use a high-intensity beam. This eliminates the need for signal averaging and the like, makes it possible to obtain a high S/N ratio, and makes it possible to carry out measurement in a short time. Furthermore, the laser light source enables narrow-linewidth wavelength sweeping; therefore, high wavelength resolution can also be achieved. In addition, the laser light is advantageous also in that the laser light is coherent light and can be focused to its diffraction limit and that high spatial resolution can also be obtained. Furthermore, in a case where an OPO or a quantum-cascade laser is used, the size of the light source 10 can be reduced, making it possible to reduce the total size of the device.

The light source 10 generates laser light 100 by converting excitation light 101, which is pulsed light shorter in wavelength than mid-infrared light and which is oscillated from a excitation light source 11, into long-wavelength light and concurrently amplifying the pulsed light through an OPO 12. Optical parametric oscillation is disclosed in, for example, Japanese Patent Application Publication, Tokukai, No. 2010-281891.

The excitation light source 11 is particularly preferably a Q-switched Nd:YAG laser (oscillation wavelength: 1.064 μm) or a Q-switched Yb:YAG laser (oscillation wavelength: 1.030 μm), each of which is capable of oscillating pulsed excitation light 101 which is shorter in wavelength than mid-infrared light. These excitation light sources are capable of allowing a switching operation to take place automatically with use of a saturable absorber. Therefore, the use of the Q-switched Nd:YAG laser or Q-switched Yb:YAG laser as the excitation light source 11 makes it possible to simplify and reduce the sizes of the excitation light source 11 and the configuration for controlling the excitation light source 11. In Q-switched oscillation, the excitation light 101 can be oscillated with, for example, a pulse width of about 8 ns at a pulse repetition frequency of 10 Hz or higher.

Figure 3:
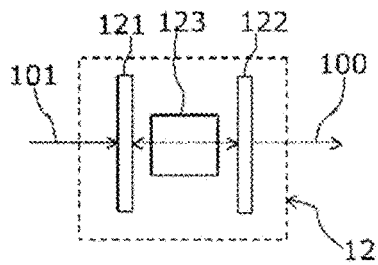
FIG. 3 schematically illustrates a configuration of an optical parametric oscillator.

FIG. 3 schematically illustrates a configuration of the OPO 12. The OPO 12 is arranged such that a non-linear optical crystal 123 is disposed between an entrance-side half mirror 121 and an exit-side half mirror 122. Excitation light 101 that has passed through the entrance-side half mirror 121 enters the non-linear optical crystal 123, is converted to light having a wavelength longer than that of the excitation light 101, and, when the light is reflected and confined between the entrance-side half mirror 121 and the exit-side half mirror 122, the light is amplified by optical parametric amplification. The amplified light passes through the exit-side half mirror 122, becomes laser light 100, and is outputted. Note that, for convenience of illustration, the direction of the laser light 100 oscillated from the OPO 12 and the direction of the excitation light 101 are different in FIG. 2; however, these directions are adjusted appropriately by using a reflector.

As the non-linear optical crystal 123, $AgGaS_2$ that is suitable for this kind of wavelength conversion is used under the condition of phase matching. By adjusting the type and matching conditions of the non-linear optical crystal 123, it is possible to adjust the wavelength (oscillation wavelength) at which the laser light 100 oscillates. As the non-linear optical crystal, it is also possible to use GaSe, $ZnGeP_2$, $CdSiP_2$, $LiInS_2$, $LiGaSe_2$, $LiInSe_2$, $LiGaTe_2$, or the like. The laser light 100 emitted from the OPO 12 has a repetition frequency and a pulse width (for example, about 8 ns) that correspond to the excitation light 101. This short pulse width achieves a high peak power of 10 W to 1 kW.

The oscillated laser light 100 is split into two portions by a beam splitter 15, and one of the two portions travels toward the sample S fixed on the sample stage 20. The other of the two portions is used for monitoring, and is detected at a monitor light detector 16. With this, even if the intensity of the laser light 100 itself changes, such a change can be recognized from output of the monitor light detector 16.

The laser light 100 which travels toward the sample S goes through a condenser lens 17 and is thereby adjusted to have a small beam spot size on the sample S and to irradiate a specific area of the sample S. The beam spot size on the sample S is, for example, preferably about 10 μm in diameter. A beam spot having such a size makes it possible to apply laser light on a per-cell basis.

The sample stage 20 has an opening that allows passage of transmitted light 100A (a transmitted portion of the laser light 100 transmitted through the sample S). The transmitted light 100A, after passing through the opening, is detected at a light detector 18. Furthermore, the sample stage 20 is capable of moving two-dimensionally relative to the optical axis of the laser light 100. This adjusts the area to be irradiated with the laser light 100 on the sample S.

There is also provided an image capturing section 21 which is for capturing an image of a region that includes the area of the ample S irradiated with the laser light 100. The image capturing section 21 is provided on the same side of the sample S as the light source 10. Note that an optical element capable of reducing the beam spot size of the laser light 100 can substituted for the condenser lens 17. A pinhole or the like may be used instead of the condenser lens 17.

A computer 30 is used to carry out overall control of the biological tissue identification system 1. The computer 30 includes a control section (tissue identification device) 31 (CPU), a display section 32, and a storage section 33. The display section 32 is a display which displays various kinds of information and measurement results. The storage section 33 is composed of a hard disk or a semiconductor memory each of which stores various kinds of data. The computer 30 also includes an input section 34 which receives user operations and which is a touchscreen, a keyboard, a mouse, and/or the like.

Figure 4:
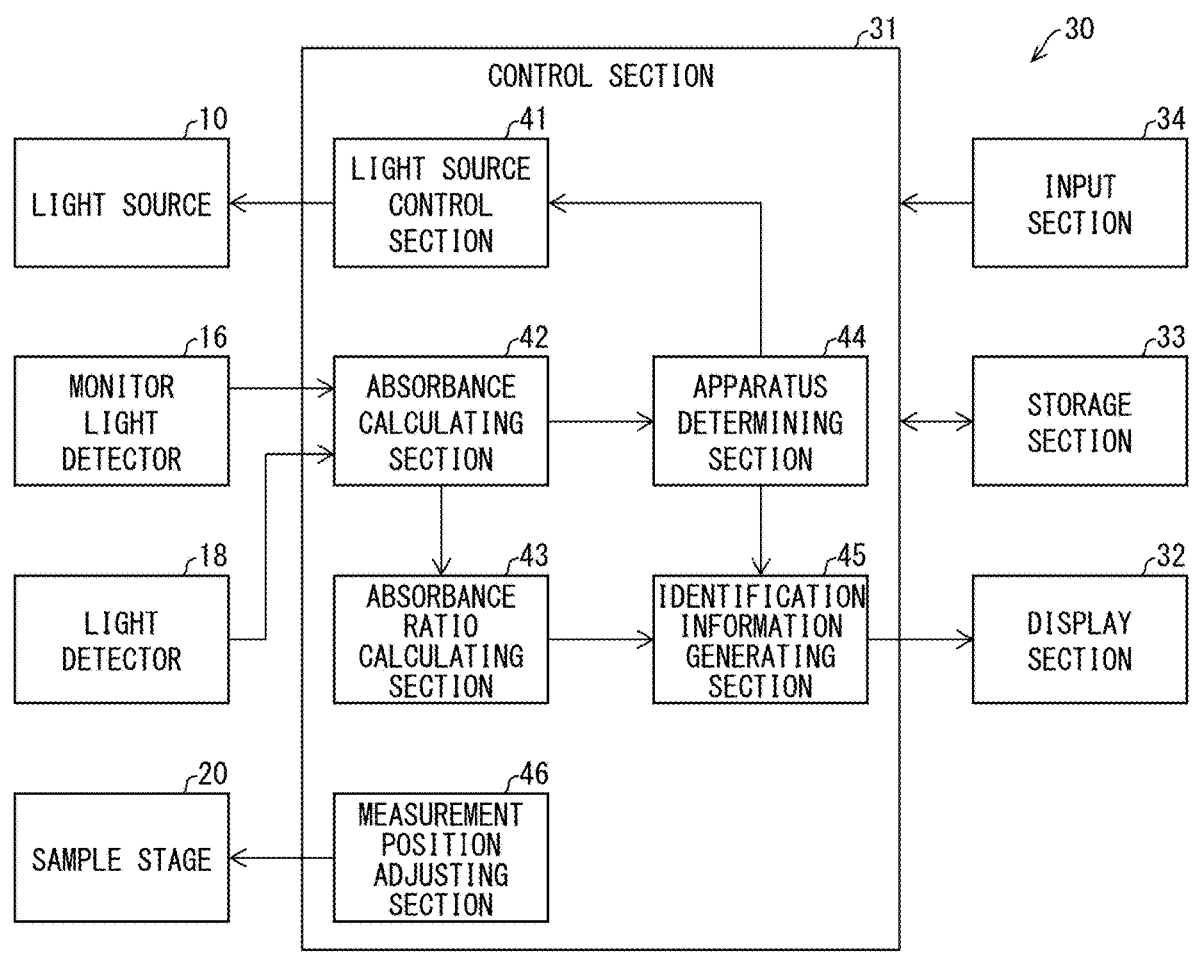
FIG. 4 is a functional block diagram illustrating a configuration of a control section.

FIG. 4 is a functional block diagram illustrating a configuration of the control section 31. As illustrated in FIG. 4, the control section 31 includes: a light source control section 41 which controls the light source 10; an absorbance calculating section 42 which calculates discrimination absorbance and reference absorbance; and an absorbance ratio calculating section 43 which calculates the ratio of discrimination absorbance to reference absorbance. The control section 31 further includes: an organ determining section 44; an identification information generating section 45; and a measurement position adjusting section 46.

The organ determining section 44 determines from which organ biological tissue in the sample S is derived, by comparing (i) an absorbance spectrum indicated by light transmitted through the biological tissue in the sample S and (ii) absorbance spectra for a plurality of pieces of tissue derived from a plurality of types of organs pre-stored in the storage section 33 (organ determination).

The identification information generating section 45 identifies the type or state of to-be-inspected biological tissue by determining within which of a plurality of preset numerical ranges the absorbance ratio falls. The identification information generating section 45 generates identification information indicative of the type or state of the biological tissue, and outputs the identification information to an output device. The output device is, for example, the display section 32, but may be any device such as a speaker or a printer, provided that a user can check the identification result via the output device.

The type of biological tissue identified by the identification information generating section 45 may mean, for example, whether the biological tissue is normal tissue, a benign tumor, or cancer tissue, or may mean the form of the biological tissue in the progress in which the biological tissue becomes cancerous (stage in the carcinogenesis process). The type of the biological tissue is not limited to cancer, and may mean the form (state) of tissue in which there is an abnormality. That is, in the present specification, determining whether the to-be-identified biological tissue contains cancer tissue or not can be considered subordinate to determining whether there is an abnormality or not in the biological tissue. Thus, the identification information generating section 45 can be said to generate identification information indicative of whether there is an abnormality or not in the biological tissue by determining within which of the plurality of numerical ranges the absorbance ratio falls.

In a case where the to-be-identified biological tissue is a tumor, the identification information generating section 45 may identify the histological type of the tumor. In a case where the to-be-identified biological tissue is cancer tissue, the identification information generating section 45 may identify whether the cancer tissue is metastatic cancer tissue or primary cancer tissue. The identification information generating section 45 may identify from which organ the to-be-identified biological tissue is derived. Carrying out each of such types of identification is included in the definition of identifying the "type" of biological tissue. The state of the biological tissue means, for example, in a case where the biological tissue is cancer tissue, the degree of malignancy of the cancer.

As such, identification in accordance with the present invention can be carried out on any type or state, provided that the type or state of biological tissue can be associated in advance with the range of values that the absorbance ratio for the biological tissue can take.

The measurement position adjusting section 46 adjusts the position of the sample stage 20 relative to the optical axis of the laser light 100. This adjustment makes it possible to adjust the position on the sample S which position is to be irradiated with the laser light 100 (i.e., measurement position).

The light detector 18 and the monitor light detector 16 can each be, for example, an HgCdTe infrared detector cooled with liquid nitrogen. The HgCdTe infrared detector is capable of receiving the laser light 100 or the transmitted light 100A whose wavelength is within the foregoing range and outputting the intensity of the received light as electrical signal. In so doing, by causing the excitation light source 11 to oscillate the excitation light 101 in the form of pulses and by extracting outputs of the light detector 18 and the monitor light detector 16 in synchronization with the pulses, it is possible to detect the laser light 100 with a high S/N ratio.

Furthermore, by recognizing in advance the relationship between the intensity detected at the monitor light detector 16 and the intensity detected at the light detector 18 when light transmittance is 100% (when the sample S is absent), even if the intensity of the laser light 100 changes over time, it is still possible to properly calculate the light transmittance of the sample S based on the intensity detected at the monitor light detector 16 and the intensity detected at the light detector 18. Note that the monitor light detector 16 is not essential in a case were the laser light 100 does not undergo significant temporal changes and the absorbance can be calculated only from the intensity detected at the light detector 18 in practice.

The above-described biological tissue identification system 1 can be realized as a microscope system. In this case, a stage of the microscope may be used as the sample stage 20. In a case where the sample S is visually checked, an objective lens and an eye lens of the microscope can be used.

(Flow of Process Carried Out by Biological Tissue Identification System 1)

Figure 5:
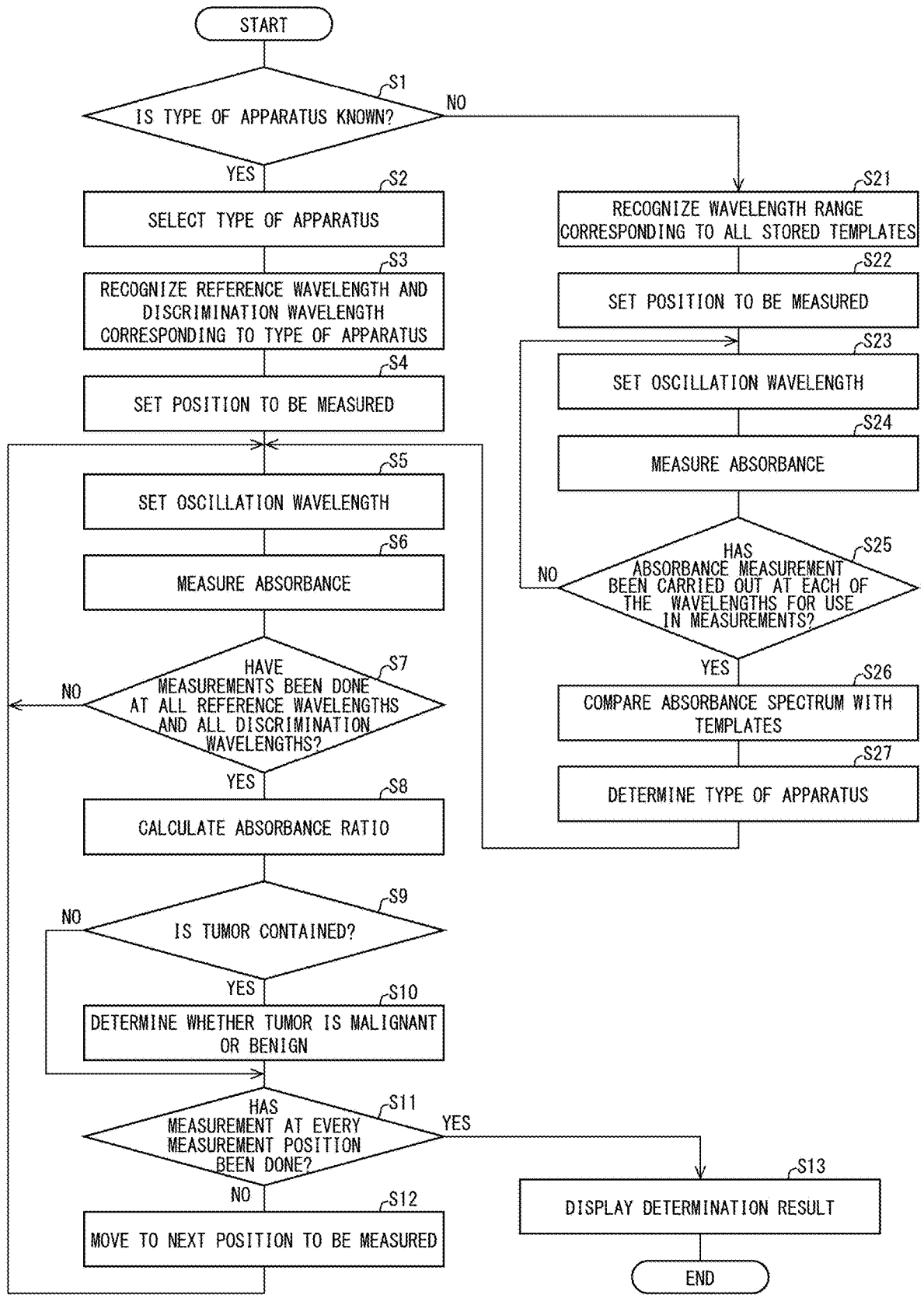
FIG. 5 is a flowchart showing an example of a flow of a process carried out by a biological tissue identification system.

FIG. 5 is a flowchart showing an example of a flow of a process carried out by the biological tissue identification system 1. The following description will discuss an example of determining which tissue, among normal tissue, adenoma, fibroadenoma, and cancer tissue, is contained in biological tissue in the sample S.

In a case where it is known that the biological tissue in the sample S is derived from a certain organ (YES in S1), the control section 31 receives, from a user via the input section 34, organ information that identifies the organ (e.g., the name of the organ, the number assigned to the organ) (S2). The organ is a group of tissue having a certain function, such as lung, stomach, muscle, brain, or the like. Pieces of organ information about various types of organs, and reference wavelengths and discrimination wavelengths for use in identifying tissue constituting the organs, are associated with each other and stored in the storage section 33.

Upon receipt of the organ information, the light source control section 41 of the control section 31 acquires, from the storage section 33, a reference wavelength and a discrimination wavelength associated with the organ information (S3). The measurement position adjusting section 46 adjusts the position of the sample stage 20, and thereby sets, to an initial position, the position to be irradiated with light of the reference wavelength and light of the discrimination wavelength (S4). Note that the adjustment of the position of the sample stage 20 (position on the sample S which position is irradiated with laser light 100) can be carried out while the user is checking, via the display section 32, an image captured by the image capturing section 21. Note that the laser light 100 whose wavelength is within the foregoing range is invisible to the eye; therefore, it is preferable to provide a light source that emits visible light during the position adjustment.

The light source control section 41 controls the light source 10 to oscillate reference inspection light (having the reference wavelength associated with the organ information) and discrimination inspection light (having the discrimination wavelength associated with the organ information) (S5: applying step). In the following description, the reference inspection light and the discrimination inspection light are each referred to as laser light 100. Part of the oscillated laser light 100 is detected at the monitor light detector 16, and the rest of the oscillated laser light 100 passes through the sample S and then is detected at the light detector 18.

The absorbance calculating section 42 recognizes signals outputted from the monitor light detector 16 and the light detector 18, and thereby calculates the absorbance of each laser light 100 by the sample S (discrimination absorbance and reference absorbance) (S6: acquiring step).

The light source control section 41 and the absorbance calculating section 42 repeat steps S5 and S6 until the application of all types of laser light 100 of all the to-be-applied wavelengths is done (S7). Upon completion of the application of all types of laser light 100 and the measurement of absorbances (YES in S7), the absorbance ratio calculating section 43 calculates the ratio of the discrimination absorbance to the reference absorbance (S8: calculating step).

The identification information generating section 45 determines within which of a plurality of numerical ranges preset for the to-be-inspected organ the absorbance ratio calculated by the absorbance ratio calculating section 43 falls, and thereby determines whether or not the biological tissue in the sample S contains a tumor (S9).

Figure 6:
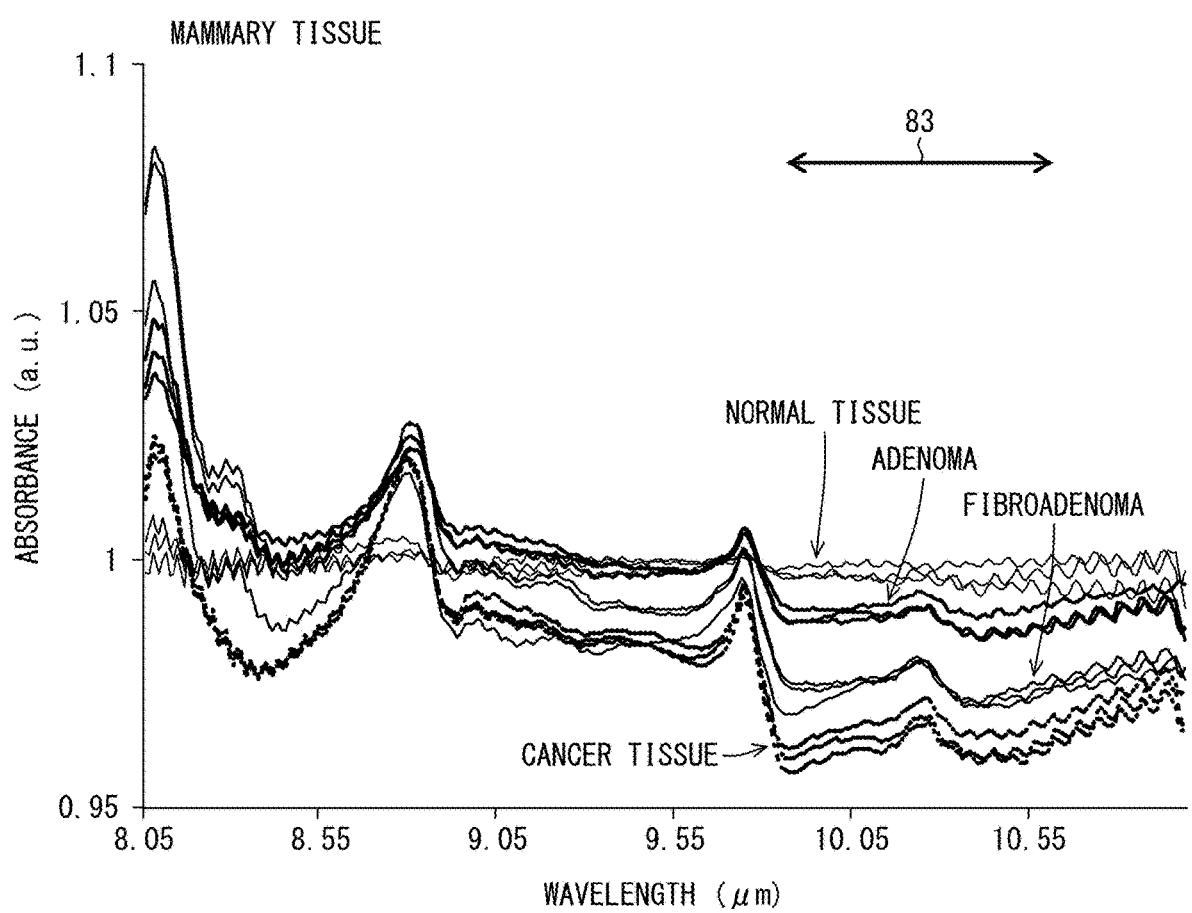
FIG. 6 is a chart showing absorbance spectra for mammary tissue.

FIG. 6 is a chart showing absorbance spectra for mammary tissue. FIG. 6 shows spectra of normal tissue, adenoma, fibroadenoma, and cancer tissue. The range represented by arrow 83 (9.80 μm to 10.60 μm), and also the ranges of from 8.05 μm to 8.15 μm, from 8.22 μm to 8.62 μm, from 8.71 μm to 8.85 μm, and from 8.88 μm to 10.6 μm, are the ranges of values that the discrimination wavelength can take. In these ranges, the absorbance differs among normal tissue, adenoma, fibroadenoma, and cancer tissue. Therefore, in a case where the organ is a mammary gland, for example, light of a wavelength of 9.75 μm can be used as a reference wavelength, and light of a wavelength of 10.05 μm can be used as a discrimination wavelength.

The range of values that the ratio of discrimination absorbance to reference absorbance (absorbance ratio) can take is preset for each of the following: normal tissue; adenoma; fibroadenoma; and cancer tissue. Such four numerical ranges are stored in the storage section 33.

In a case where the absorbance ratio calculated by the absorbance ratio calculating section 43 falls within a numerical range that is associated with any of the following: adenoma; fibroadenoma; and cancer tissue, the identification information generating section 45 determines that the biological tissue contains a tumor (YES in S9 of FIG. 5). The identification information generating section 45 further determines within which of the numerical ranges associated with adenoma, fibroadenoma, and cancer tissue the absorbance ratio calculated by the absorbance ratio calculating section 43 falls, and thereby determines whether the tumor is malignant (the tumor is cancer tissue) or benign (S10). The identification information generating section 45 may further determine whether the tumor is adenoma or fibroadenoma.

Note that the identification information generating section 45 may carry out steps S9 and S10 as a single step and thereby determine whether the biological tissue is normal tissue, adenoma, fibroadenoma, or cancer tissue in one step. Alternatively, the following arrangement may be employed: normal tissue, adenoma, and fibroadenoma are treated as tissue which is not cancer tissue; and the identification information generating section 45 only determines whether or not the sample S contains cancer tissue. Alternatively, the following arrangement may be employed: adenoma, fibroadenoma, and cancer tissue are treated as tumor tissue; and the identification information generating section 45 only determines whether or not the sample S contains tumor tissue.

Upon completion of the absorbance measurement and determination at the initially set measurement position, the measurement position adjusting section 46 causes the sample stage 20 to move and changes the measurement position (S11, S12).

Upon completion of the absorbance measurement and determination at every measurement position (YES in S11), the identification information generating section 45 generates identification information indicative of the type of the biological tissue, and outputs the identification information to the display section 32 (S13: outputting step).

On the contrary, in a case where it is unknown from which organ the biological tissue in the sample S is derived (NO in S1), steps S21 to S27 (organ determining step) are carried out. Specifically, the organ determining section 44 compares an absorbance spectrum of the biological tissue in the sample S with each of absorbance spectra (templates) of a plurality of types of organs pre-stored in the storage section 33, and thereby determines from which organ the biological tissue in the sample S is derived. Note that the invention relating to steps S21 to S27 can be regarded as an invention independent of the invention relating to steps S2 to S13.

Figure 7:
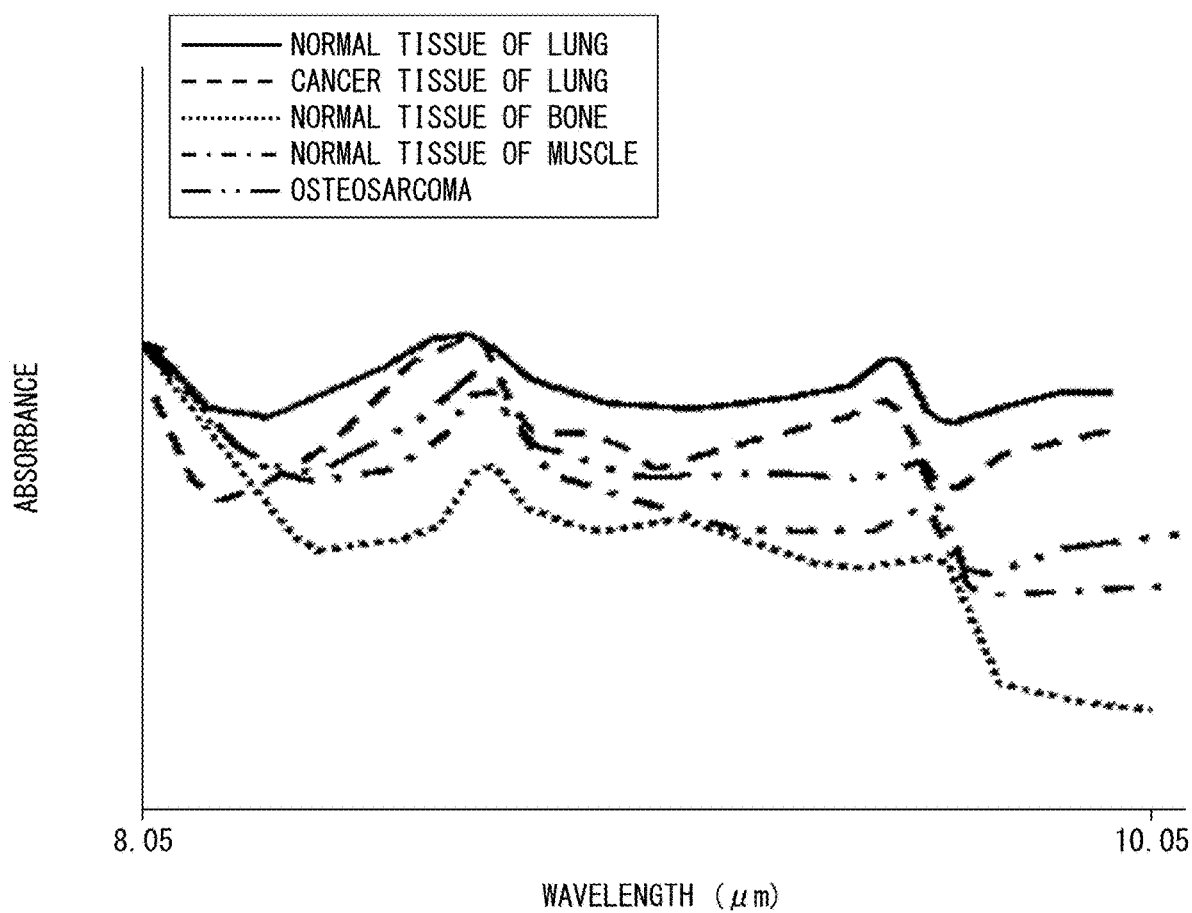
FIG. 7 is a chart showing an example of templates for use in determining from which organ biological tissue is derived.

FIG. 7 is a chart showing an example of templates for use in determining from which organ the biological tissue is derived. FIG. 7 shows smoothed versions of absorbance spectra of (1) normal tissue of lung, (2) cancer tissue of lung, (3) normal tissue of bone, (4) normal tissue of muscle, and (5) osteosarcoma. These templates, and data indicative of wavelength ranges of the respective templates, are pre-stored in the storage section 33.

In the organ determining step, first, the light source control section 41 recognizes, from the storage section 33, a wavelength range corresponding to all the templates (in the example shown in FIG. 7, the range of 8.05 μm to 10.05 μm) (S21 in FIG. 5). Then, the position to be measured is set in a similar manner to S4 (S22).

The light source control section 41 controls the light source 10 to set the oscillation wavelength of the light source 10 to one of the wavelengths in the wavelength range corresponding to a first template (S23).

The absorbance calculating section 42 calculates an absorbance by recognizing output signals from the monitor light detector 16 and the light detector 18 (S24). The wavelength set in S23 is one of many wavelengths in the wavelength ranges corresponding to the respective templates. The absorbance measurement is carried out on each of these many wavelengths (S25). With this, an absorbance spectrum that can be compared with the templates is obtained. In order to efficiently obtain an absorbance spectrum in such a broad range, it is preferable to use, as the light source 10, a light source including a quantum-cascade laser whose oscillation wavelength is adjustable in a mid-infrared region or a light source including an OPO (optical parametric oscillator) 12.

The organ determining section 44 compares the absorbance spectrum obtained by the above-described measurement with each of the templates, and finds the template which is least different from the absorbance spectrum (S26). Any of known techniques can be used to carry out matching between the measured absorbance spectrum and templates. Then, the organ determining section 44 outputs, to the light source control section 41 and the identification information generating section 45, organ information indicative of the organ corresponding to the found template (S26). The flow of the subsequent steps is the same as the flow of the foregoing steps S5 to S13.

The organ determining section 44 does not necessarily need to output a single-meaning determination result. The organ determining section 44 may output, for example, organ information indicative of a plurality of candidate organs whose difference from the measured absorbance spectrum falls within a predetermined range.

The contrast of the absorbance may vary depending on conditions in which the measurement is carried out or the conditions (such as thickness) of the sample S. To address this, in a case of carrying out the matching, the spectral form may be corrected. For example, the measured absorbance spectrum may be corrected so that the difference between the maximum value and the minimum value of the measured absorbance spectrum is equal to the difference between the maximum value and the minimum value of a template.

As such, the presence of the organ determining section 44 makes it possible, even in cases of an unknown sample S, to identify biological tissue contained in the sample S. Furthermore, even in a case where cancer tissue derived from second tissue is present in first tissue, it is possible to appropriately identify such tissue.

Note that the organ determining section 44 may carry out organ determination by comparing (i) an absorbance spectrum indicated by light reflected from the biological tissue in the sample S and (ii) absorbance spectra pre-stored in the storage section 33.

The organ determining section 44 may carry out organ determination with use of a transmittance spectrum indicated by light transmitted through the biological tissue in the sample S or a reflectance spectrum indicated by light reflected from the biological tissue in the sample S, instead of the foregoing absorbance spectrum. In this case, it is only necessary that a template(s) of a transmittance spectrum (spectra) be stored in the storage section 33 when transmittance is used or that a template(s) of a reflectance spectrum (spectra) be stored in the storage section 33 when reflectance is used.

The organ determining section 44 may carry out organ determination on a single position on the sample S or may carry out organ determination on a plurality of positions on the sample S. Furthermore, the organ determining section 44 and the identification information generating section 45 may carry out determination on the same position.

The organ determining section 44 may determine which type or state is a candidate for the type or state of the biological tissue, by comparing (i) the measured absorbance spectrum and (ii) pre-stored absorbance spectra for a plurality of types of tissue in a single organ. For example, the following arrangement may be employed: the organ determining section 44 provisionally determines whether the biological tissue in the sample S is normal tissue of lung or cancer tissue of lung like the example shown in FIG. 7; and the identification information generating section 45 makes a final identification with use of the absorbance ratio. Furthermore, in a case of the intestinal tract, the organ determining section 44 may determine which of a plurality of types of tissue in the intestinal tract, e.g., epithelial tissue (mucus membrane), connective tissue, muscular tissue and the like, is a candidate for the biological tissue. That is, the organ determining section 44 determines which type or state is a candidate for the type or state of the to-be-inspected biological tissue. In such cases, in S27 in FIG. 5, the organ determining section 44 outputs information indicative of the candidate to the light source control section 41 and the identification information generating section 45. The storage section 33 pre-stores therein the candidate, a reference wavelength, a discrimination wavelength, and the foregoing plurality of numerical ranges for identification.

In the above-described flow, the identification information generating section 45 acquires, from the user or the organ determining section 44, the organ information indicating from which organ the biological tissue in the sample S is derived, and carries out the determination with use of the plurality of numerical ranges for the organ indicated by the organ information. Note, however, that the identification information generating section 45 may determine from which organ the biological tissue in the sample S is derived by determining within which of a plurality of preset numerical ranges the absorbance ratio falls. In this case, the organ determining section 44 is not essential.

(Example of how Identification Information is Displayed)

(a) of FIG. 8 shows an example of an image of a sample S. (b) of FIG. 8 shows an example of an image in a case where identification information generated by the identification information generating section 45 is displayed on the display section 32. In the image of the biological tissue shown in (a) of FIG. 8, cancer tissue 90 is present. In the example shown in (b) of FIG. 8, the biological tissue identification system 1 divides the biological tissue into segments 91 each having a size of 500 µm×500 µm, and measures the absorbance on a per-segment-91 basis. In S12 of FIG. 5, the measurement position adjusting section 46 moves the position of the sample stage 20 so that all the segments 91 are measured for absorbance.

As the size of each segment 91 decreases, the accuracy of tissue identification increases. Therefore, each segment 91 preferably has a size of about 10 µm×10 µm.

(Case where a Plurality of Reference Wavelengths are Used and/or a Plurality of Discrimination Wavelengths are Used)

In a case where (i) a plurality of reference wavelengths and a discrimination wavelength are used, (ii) a reference wavelength and a plurality of discrimination wavelengths are used, or (iii) a plurality of reference wavelengths and a plurality of discrimination wavelengths are used, the absorbance calculating section 42 calculates a plurality of absorbance ratios and the identification information generating section 45 determines within which of predetermined numerical ranges each absorbance ratio falls.

Table 1 shows specific examples of a threshold for use for each combination of (i) the reference wavelength A (8.74 µm) or the reference wavelength B (9.73 µm) in the example shown in FIG. 1 and (ii) the discrimination wavelength A (8.28 µm) or the discrimination wavelength B (9.26 µm) in the example shown in FIG. 1. The threshold is the value at the border between the range of absorbance ratios for normal tissue and the range of absorbance ratios for cancer tissue.

TABLE 1

|  | Reference wavelength A | Reference wavelength B |
| --- | --- | --- |
| Discrimination wavelength A | 0.9858 | 0.9905 |
| Discrimination wavelength B | 0.9860 | 0.9907 |

For example, in a case where the reference wavelength A and the discrimination wavelength B are used, the identification information generating section 45 determines that the biological tissue is cancer tissue if the absorbance ratio calculated by the absorbance ratio calculating section 43 is smaller than 0.9860.

In a case where the identification results based on the absorbance ratios (e.g., whether the biological tissue is normal tissue or cancer tissue) are different from each other, the identification information generating section 45 may output the identification result "cancer tissue" unless all the identification results are "normal tissue" or may output, as identification information, a value indicative of the ratio between the number of the identification results "normal tissue" and the number of the identification results "cancer tissue".

Alternatively, the identification information generating section 45 may calculate a score indicative of the degree of certainty of the identification result obtained based on each absorbance ratio. The score can be, for example, a value indicative of how far the measured absorbance ratio is from the border between numerical ranges (threshold). The identification information generating section 45 may employ an identification result which is considered more reliable. For example, the identification information generating section 45 may employ an identification result which is based on an absorbance ratio with a higher score.

(Specific Examples of Absorbance Spectrum)

FIG. 9 is a chart showing absorbance spectra of normal tissue and cancer tissue (histiocytic sarcoma) in liver tissue. In the example shown in FIG. 9, a reference wavelength is 9.75 µm, and a discrimination wavelength range is 9.33 µm to 9.64 µm. FIG. 10 is a chart showing absorbance spectra of cancer tissue (hepatocellular cancer) and lymphocyte in the liver. In the example shown in FIG. 10, a reference wavelength is 9.75 µm, and discrimination wavelength ranges are 8.05 µm to 8.40 µm and 8.85 µm to 9.56 µm. FIG. 11 is a chart showing absorbance spectra of normal tissue of muscle, normal tissue of bone, and cancer tissue (osteosarcoma). In the example shown in FIG. 11, a reference wavelength is 9.77 µm, and a discrimination wavelength range is 8.05 µm to 10.5 µm. FIG. 12 is a chart showing absorbance spectra of normal tissue and cancer tissue (medulloblastoma) in the cerebellum. In the example shown in FIG. 12, a reference wavelength is 9.71 µm, and a discrimination wavelength range is 8.05 µm to 10.5 µm. FIG. 13 is a chart showing absorbance spectra of normal tissue and cancer tissue (malignant lymphoma) in the liver. In the example shown in FIG. 13, a reference wavelength is 9.75 µm, and discrimination wavelength ranges are 9.07 µm to 9.77 µm and 9.82 µm to 10.8 µm. FIG. 14 is a chart showing absorbance spectra of normal tissue and cancer tissue (rhabdomyosarcoma) of muscle. In the example shown in FIG. 14, a reference wavelength is 8.75 µm, and discrimination wavelengths ranges are 8.20 µm to 8.66 µm and 8.91 µm to 11.0 µm. FIG. 15 is a chart showing absorbance spectra of normal tissue and cancer tissue (histiocytic sarcoma) in the spleen. In the example shown in FIG. 15, a reference wavelength is 9.76 µm, and discrimination wavelength ranges are 8.05 µm to 8.39 µm, 8.70 µm to 9.58 µm, and 9.87 µm to 10.9 µm.

It is apparent from these results that, for every organ, the absorbance spectrum differs significantly depending on the type or state of biological tissue, in the discrimination wavelength range represented by arrow 83. It is possible to identify the type or state of the biological tissue by setting a reference wavelength, a discrimination wavelength, and the range of values that the absorbance ratio can take according to the type of organ or according to the purpose of identification. The reference wavelength, the discrimination wavelength, and the range of absorbance ratios can be set by: acquiring absorbance spectra of to-be-inspected biological tissue of various types; and comparing the acquired absorbance spectra.

Embodiment 2

The following description will discuss another embodiment of the present invention. For convenience of description, members having functions identical to those described in Embodiment 1 are assigned identical referential numerals, and their descriptions are omitted here.

FIG. 16 illustrates a configuration of a biological tissue identification system 2 in accordance with Embodiment 2. According to the biological tissue identification system 2, the absorbance calculating section 42 calculates an absorbance indicated by reference inspection light reflected from biological tissue and an absorbance indicated by discrimination inspection light reflected from the biological tissue. The algorithm of tissue identification is the same as that of the biological tissue identification system 1. The control section 31 may calculate the ratio of a reflectance indicated by discrimination inspection light reflected from the biological tissue to a reflectance indicated by reference inspection light reflected from the biological tissue, instead of the absorbance ratio.

In the biological tissue identification system 2, one of the two portions of laser light 100 split by the beam splitter 15 is applied to the sample S fixed on the sample stage 20, and a reflected portion of the laser light 100 reflected from the sample S (such a reflected portion is "reflected light 100B") is detected by the light detector 18. Also in such a case in which reflected light is used, it is possible to appropriately carry out identification of biological tissue.

Embodiment 3

The following description will discuss a further embodiment of the present invention. (a) of FIG. 17 is a cross-sectional view illustrating a configuration of an endoscope system 3 which is applicable to the biological tissue identification system 1 or the biological tissue identification system 2. As illustrated in (a) of FIG. 17, the endoscope system 3 applies reference inspection light and discrimination inspection light to biological tissue and receives reflected light from the biological tissue.

The endoscope system 3 includes: a measuring head 50 for use near a living body L; a light source (first light source) 10; and an illuminating light source (second light source) 70. The illuminating light source 70 is a light source which emits visible light (illuminating light 200) for optical observation of a to-be-measured area of the living body L through an image capturing section 21.

The body (i.e., tube 60) of the measuring head 50 contains therein a light detector (first light receiving section) 18, the image capturing section (second light receiving section) 21, and end portions of an inspection optical fiber (first optical fiber) 51 and an illuminating optical fiber (second optical fiber) 54, which are arranged in the order named in the direction from the tip of the tube 60. The inspection optical fiber 51 is an optical fiber which guides laser light 100 emitted from the light source 10. The laser light 100, after propagating through the inspection optical fiber 51, is applied to the living body L through a condenser lens 17 provided on a side wall of the tube 60. The illuminating optical fiber 54 is an optical fiber which guides illuminating light 200 emitted from the illuminating light source 70. The illuminating optical fiber 54 is arranged coaxial with the inspection optical fiber 51, and covers the outer surface of the inspection optical fiber 51. The illuminating light 200, after propagating through the illuminating optical fiber 54, is applied to the living body L through the condenser lens 17. The illuminating light 200 does not need to be laser light, and the illuminating optical fiber 54 does not need to be as high in propagation characteristics as the inspection optical fiber 51.

The image capturing section 21 is constituted by an image pickup device 211 and an objective lens 212 provided on the side wall of the tube 60. A reflected portion of the illuminating light reflected from the to-be-measured area of the living body L is received by the image pickup device 211 through the objective lens 212, and thereby an image of the to-be-measured area is captured. A signal outputted from the image pickup device 211 is transmitted to the display section 32, which allows a user to position the measuring head 50 while viewing a screen of the display section 32.

The light detector 18 receives reflected light (diffused reflected light) 100B, which is a reflected portion of the laser light 100, from the living body L. The reflected light 100B is light that penetrated into the biological tissue, was reflected by the biological tissue during the penetration, and thereby traveled out of the biological tissue. The reflected light 100B enters the light detector 18 through an objective lens 52 on the side wall of the tube 60 and through a light-receiving optical fiber 53. The magnification of the objective lens 52 is different from that of the condenser lens 17. A signal outputted from the light detector 18 is transmitted to the control section 31 of the biological tissue identification system 1 or of the biological tissue identification system 2. The light detector 18 can be a small light detector, such as a pyroelectric infrared detector.

(b) of FIG. 17 illustrates the side wall of the tube 60. As illustrated in (b) of FIG. 17, the objective lens 52 corresponding to the light detector 18, the objective lens 212 of the image pickup device 211, and the condenser lens 17 located at the exit-side end of the inspection optical fiber 51 (and illuminating optical fiber 54) are arranged close to each other in the order named in the direction from the tip of the tube 60. Such a manner of arrangement makes it possible to capture an image of the area irradiated with the laser light 100 and also possible to receive a reflected portion of the laser light 100 reflected from the living body L.

Note, however, that the manner in which the light detector 18, the image pickup device 211, the inspection optical fiber 51, and the illuminating optical fiber 54 are arranged in the tube 60 is not limited to that described above. For example, the relative positons of (i) the inspection optical fiber 51 and the illuminating optical fiber 54 and (ii) the light detector 18 can be switched.

(Effect of Endoscope System 3)

With use of the endoscope system 3 including the measuring head 50, it is possible to apply laser light 100 to an intended area of the living body L and noninvasively identify biological tissue utilizing a reflected portion of the laser light 100 reflected from the living body L. The measuring head 50 is flexible; therefore, with use of the measuring head 50 which is small in size, it is possible to insert the measuring head 50 into various types of organs of the living body, and thus possible to identify tissue in those organs.

Furthermore, since the inspection optical fiber 51 and the illuminating optical fiber 54 are arranged coaxially with each other, it is possible to unfailingly apply illuminating light to an area irradiated with inspection light (i.e., area to be measured). This ensures that the user can see the area to be measured.

Embodiment 4

The following description will discuss still a further embodiment of the present invention. A biological tissue identification system 1a in accordance with Embodiment 4 is different from the biological tissue identification system 1 in that the biological tissue identification system 1a includes an objective mirror (not illustrated, also called "reflective objective lens") instead of the condenser lens 17. The objective mirror includes a reflector therein, and focuses laser light 100 by reflecting the laser light 100 at the reflector. The use of such an objective mirror makes it possible to reduce the diameter of the laser light 100.

In the biological tissue identification system 1a, the laser light 100 focused by the objective mirror is applied to the sample S (applying step), and transmitted light 100A (transmitted portion of the laser light 100 transmitted through the sample S) or reflected light 100B (reflected portion of the laser light 100 reflected from the sample S) is received by the light detector 18 (receiving step).

The objective mirror is, for example, an objective mirror of Schwarzschild type which is constituted by reflecting surfaces of metal coatings. The NA of the objective mirror is, for example, 0.3, and the focal length of the objective mirror is, for example, 13.3 mm.

The biological tissue identification system 1a includes the objective mirror, and therefore is capable of further reducing the beam spot size compared to a case where the condenser lens 17 is used. With this, the irradiated region of the sample S irradiated with the laser light 100 decreases in size, that is, the segments 91 decrease in size. This makes it possible to increase the number of segments 91 per unit area. For example, in a case where the biological tissue identification system 1 is used, the segments 91 each have a size of 500 μm×500 μm, whereas, in a case where the biological tissue identification system 1a is used, segments 91 each having a size of about 70 μm×70 μm can be achieved. Thus, the use of the biological tissue identification system 1a makes it possible to obtain a more detailed (higher-resolution) identification result.

The following description discusses an example in which a high-resolution identification result was obtained, with reference to FIG. 18. In the example shown in FIG. 18, liver tissue is used as the sample S. (a) of FIG. 18 shows identification information outputted by the biological tissue identification system 1. (b) of FIG. 18 is an image of the liver tissue which is to be identified. (c) of FIG. 18 is the image of the liver tissue on which another image (i.e., identification information provided by the biological tissue identification system 1a) is superimposed. (d) of FIG. 18 is an enlarged view of a part of the image of the liver tissue enclosed by solid line in (c) of FIG. 18.

Note here that (a) of FIG. 18 shows identification results for the part enclosed by solid line in (b) of FIG. 18, and (c) of FIG. 18 shows identification results for the part enclosed by dashed line in (b) of FIG. 18. The part enclosed by dashed line in (d) of FIG. 18 is an area which has been pathologically diagnosed as cancer tissue (area infiltrated with malignant lymphoma cells). Note that the identification results shown in (a) and (c) of FIG. 18 are those obtained with use of the same sample, and the images shown in (b) and (d) of FIG. 18 are those obtained by staining a sample taken from the vicinity of the above-mentioned sample.

As shown in (a) to (c) of FIG. 18, in a case where the biological tissue identification system 1a is used, the segments 91 are smaller in size and therefore larger in number than in the case where the biological tissue identification system 1 is used. Thus, a detailed identification result was obtained. Furthermore, a comparison between (c) of FIG. 18 and (d) of FIG. 18 shows that the shape of the area which has been determined by the identification information generating section 45 as being highly likely to be "cancer tissue" and the shape of the area which has been diagnosed as cancer tissue based on a histopathological image are substantially the same. That is, the biological tissue identification system 1a has more improved resolution than the biological tissue identification system 1, and is capable of obtaining a highly accurate identification result. With this, the biological tissue identification system 1a is capable of, even if cancer tissue is very small, accurately identifying the position and shape of the cancer tissue.

The identification information generating section 45 may output, to the display section 32, the results of tissue determination as an image so that, as shown in (c) of FIG. 18, each segment 91 is displayed in a color that corresponds to the result of tissue determination on that segment 91 and thereby the results of tissue determination are visually perceivable as an image of the tissue.

An object of the invention in accordance with Embodiment 4 is to increase the accuracy of measurement of the transmittance, reflectance, or absorbance of light applied to biological tissue. This is described below.

FIG. 19 illustrates the waveforms of pulses obtained during oscillation of laser light 100. The light source 10 of the biological tissue identification system 1a oscillates pulsed laser light 100. The inventors measured the waveforms of pulses when the light source 10 oscillated the laser light 100, with use of a photodetector. Specifically, the inventors used the photodetector to convert the laser light 100 emitted by the light source 10 into electrical signal, and observed the electrical signal with an oscilloscope.

As illustrated in FIG. 19, the laser light 100 oscillated by the light source 10 contains a main pulse 300 and a subpulse 301. The main pulse 300 is a main component of the laser light 100. The subpulse 301 is an inevitably generated pulse accompanying the main pulse 300.

The same measurement was carried out a plurality of times, and it was found that the intensity of the subpulse 301 varies from one wavelength to another or changes each time the measurement is carried out. Furthermore, when an absorbance was calculated in the biological tissue identification system 1, temporal integration was carried out on laser light including all the main pulses 300 and subpulses 301. These demonstrate that the subpulse 301 can affect the result of measurement of absorbance (transmittance or reflectance) as noise.

In view of above, in order to reduce the effect of the subpulse 301 on the measurement result and improve the accuracy of measurement, the inventors have achieved a method in which (i) transmitted light 100A (or reflected light 100B) derived from the main pulse 300 is detected by the light detector 18 and (ii) transmitted light 100A (or reflected light 100B) derived from the subpulse 301 is not detected by the light detector 18.

Specifically, the following describes an inspection method in accordance with Embodiment 4. The inventors set a time gate width 304, i.e., the time for which the light detector 18 is allowed to detect only the transmitted light 100A (or the reflected light 100B), and limited the time for which the light detector 18 is allowed to receive light. The time gate width 304 is set such that the time gate width 304 is equal to or longer than a pulse width 302 of the main pulse 300. With this, the biological tissue identification system 1a calculates an absorbance by carrying out temporal integration of only main pulses 300.

For ensuring that the main pulse 300 in its entirety will be measured, the time gate width 304 is set such that the time gate width 304 contains not only the pulse width 302 but also times before and after the pulse width 302 (i.e., the times represented by arrows 303 in FIG. 19). Each time represented by arrow 303 is preferably set such that the time does not contain the time during which the subpulse 301 is generated. Specifically, each of the times represented by arrows 303 in FIG. 19 need only be set to about 0% to 10% of the pulse width 302, e.g., 3% of the pulse width 302.

Note that the point in time at which the light source 10 oscillates the laser light 100 and the point in time at which the light detector 18 detects the transmitted light 100A are not exactly the same. Therefore, the points in time at which the light detector 18 is allowed to receive light need only be set in consideration of the above-mentioned difference between points in time.

Also note that Embodiment 4 is not intended for completely avoiding the detection of the subpulse 301. The subpulse 301 may be detected, provided that tissue identification is not affected. That is, in Embodiment 4, it is only necessary that the time gate width 304 be set so that at least part of the subpulse 301 is not detected by the light detector 18.

Furthermore, in a case where the pulse width 302 is the same among all wavelengths for use in measurements, the measurements may be carried out with use of a fixed time gate width 304 for all those wavelengths. However, in a case where the pulse width 302 differs from one wavelength to another, the time gate width 304 is preferably changed on a per-wavelength basis as necessary.

FIG. 20 is a functional block diagram illustrating a configuration of a control section 31a of the biological tissue identification system 1a in accordance with Embodiment 4. Except for the control section 31a, the biological tissue identification system 1a is the same in configuration as the biological tissue identification system 1.

As illustrated in FIG. 20, the control section 31a of the computer 30 controls the light detector 18 to detect the transmitted light 100A or the reflected light 100B only in the duration of the foregoing time gate width 304. With this, the biological tissue identification system 1a is capable of obtaining an identification result less affected by the subpulse 301, i.e., noise. That is, it is possible to further improve the accuracy of tissue identification.

The configuration discussed in Embodiment 4 is one in which the objective mirror and the control section 31a are employed in the configuration of the biological tissue identification system 1. Such a configuration is also applicable to Embodiments 2 and 3, and such Embodiments 2 and 3 also provide a similar effect.

(Effect of Biological Tissue Identification System 1a)

The biological tissue identification system 1 and the biological tissue identification system 1a were used to measure absorbance spectra of normal liver and an area infiltrated with malignant lymphoma cells in liver tissue. Note that, in this measurement, the pulse width 302 for all wavelengths for use in the measurement was 557 ns, and the time gate width 304 was fixed at 590 ns (the sum of the pulse width 302 and 3% of the pulse width 302 at each edge of the pulse). Each tissue was subjected to the measurement a plurality of times. FIG. 21 shows charts showing the absorbance spectra of normal liver and an area infiltrated with malignant lymphoma cells in liver tissue. (a) of FIG. 21 shows absorbance spectra obtained with use of the biological tissue identification system 1, and (b) of FIG. 21 shows absorbance spectra obtained with use of the biological tissue identification system 1a. Note that the absorbance spectra shown in (a) and (b) of FIG. 21 were obtained by measuring the same sample.

As shown in (b) of FIG. 21, the difference between the normal liver and the area infiltrated with malignant lymphoma cells is more apparent in the results of measurement carried out by the biological tissue identification system 1a than in the results of measurement carried out by the biological tissue identification system 1 shown in (a) of FIG. 21. That is, it was confirmed that, in the biological tissue identification system 1a, the resolution is improved by the presence of the objective mirror, the effect of the subpulse 301 is reduced by setting the time gate width 304, and therefore the accuracy of measurement of absorbance spectra is improved.

In particular, as shown in (a) of FIG. 21, in the case of measurement using the biological tissue identification system 1, for example, when the measurement was carried out with use of light of a wavelength of 9.83 µm, the absorbance of normal tissue varied greatly each time it was measured, and the result of tissue identification was indefinite. Furthermore, when the measurement was carried out with use of light of a wavelength 9.07 µm, the difference in absorbance between the normal tissue and the area infiltrated with malignant lymphoma cells was small. In contrast, as shown in (b) of FIG. 21, in the case of measurement using the biological tissue identification system 1a, when the measurement was carried out with use of light of a wavelength of 9.83 µm, the variation in absorbance of the normal tissue among measurements was small. Furthermore, when the measurement was carried out with use of light of a wavelength of 9.07 µm, the difference between the normal liver and the area infiltrated with malignant lymphoma cells was clearly recognizable.

(Specific Examples of Absorbance Spectrum)

Examples of measurements which were carried out using the biological tissue identification system 1a are discussed below with reference to FIGS. 22 to 29. Note that each tissue was subjected to measurement a plurality of times. FIG. 22 is a chart showing absorbance spectra of a plurality of different types of tissue and cancer tissue. In the example shown in FIG. 22, the measurement was carried out on bone marrow, rhabdomyosarcoma (cancer tissue), muscle, and bone, and a reference wavelength is 8.84 µm and a discrimination wavelength range is 8.87 µm to 9.02 µm. FIG. 23 is a chart showing absorbance spectra of normal tissue, cancer tissue, and lymphocyte in liver tissue. In the example shown in FIG. 23, a reference wavelength is 9.75 µm and a discrimination wavelength range is 9.10 µm to 9.55 µm. FIG. 24 is a chart showing absorbance spectra of normal tissue, primary lung cancer tissue, and a lesion of pulmonary metastasis of liver cancer in lung tissue. In the example shown in FIG. 24, a reference wavelength is 9.70 µm and a discrimination wavelength range is 9.75 µm to 10.00 µm.

FIG. 25 is a chart showing absorbance spectra of normal tissue and a cardiac infarct area in heart tissue. In the example shown in FIG. 25, a reference wavelength is 8.76 µm and discrimination wavelength ranges are 9.18 µm to 9.71 µm and 9.84 µm to 11.00 µm. FIG. 26 is a chart showing absorbance spectra of normal tissue and tissue of fatty liver in liver tissue. In the example shown in FIG. 26, a reference wavelength is 9.75 µm and a discrimination wavelength range is 8.05 µm to 9.18 µm. FIG. 27 is a chart showing absorbance spectra of normal tissue and tissue of liver cirrhosis in liver tissue. In the example shown in FIG. 27, a reference wavelength is 9.75 µm and discrimination wavelength ranges are 8.61 µm to 9.00 µm and 9.05 µm to 9.26 µm.

FIG. 28 is a chart showing absorbance spectra of normal tissue, radiation-induced cancer tissue, and spontaneous cancer tissue in cerebellar tissue (medulloblastoma). In the example shown in FIG. 28, a reference wavelength is 9.71 µm and discrimination wavelength ranges are 8.80 µm to 9.34 µm and 9.89 µm to 10.25 µm. FIG. 29 is a chart showing absorbance spectra of a normal renal tubule and a glomerulus with amyloid deposition in kidney tissue. In the example shown in FIG. 29, a reference wavelength is 9.73 µm, and a discrimination wavelength range is 8.88 µm to 9.14 µm.

In each of the results shown in FIGS. 22 to 29, it is apparent that the absorbance spectrum differs significantly depending on the type or state of biological tissue, in the discrimination wavelength ranges represented by arrows 83, 83A, and 83B. The results shown in FIG. 22 indicate that it is possible to identify cancer tissue in a plurality of types of tissue.

The absorbance spectra shown in the example of in FIG. 23 are those obtained using samples whose border between normal tissue, cancer tissue, and lymphocyte is unclear in histopathological images. The results shown in FIG. 23 indicate that, even in a case where the border between different types of tissue is unclear, it is possible to identify each tissue in the discrimination wavelength range represented by arrow 83.

Furthermore, the results shown in FIG. 24 indicate that, in the discrimination wavelength range represented by arrow 83, it is possible to identify normal tissue and cancer tissue and also identify from which tissue the cancer tissue is derived. For example, it is possible to identify whether the cancer tissue is metastatic cancer tissue or primary cancer tissue.

Furthermore, the results shown in FIG. 25 indicate that it is possible to identify normal tissue and a cardiac infarct area in the discrimination wavelength ranges represented by arrows 83A and 83B. The results indicate that, in particular, in a case where the measurement is carried out with use of light of a wavelength of 9.62 µm, it is possible to precisely identify the cardiac infarct area.

The results shown in FIGS. 26 and 27 indicate that it is possible to identify normal tissue and tissue of fatty liver in the discrimination wavelength range represented by arrow 83 in FIG. 26 and possible to identify normal tissue and tissue of liver cirrhosis in the discrimination wavelength ranges represented by arrows 83A and 83B in FIG. 27. In addition, as described earlier, it is also possible to identify normal tissue and cancer tissue in liver tissue.

With regard to liver tissue, normal tissue becomes fatty liver when lipid droplets accumulate in hepatocytes, whereas the normal tissue becomes liver cirrhosis when fibrosis occurs due to collagen depositions. Furthermore, liver cancer may originate from the liver cirrhosis. In Embodiment 4, it is possible to identify in which stage the carcinogenesis process in the liver tissue is.

The results shown in FIG. 28 indicate that, in the discrimination wavelength ranges represented by arrows 83A and 83B, it is possible to identify normal tissue and cancer tissue and also identify whether the cancer tissue is spontaneous cancer tissue or radiation-induced cancer tissue. It has been difficult to distinguish between radiation-induced cancer tissue and spontaneous cancer tissue in a histopathological image; however, in Embodiment 4, it is possible to identify such types of cancer tissue.

The results shown in FIG. 29 indicate that, in the discrimination wavelength range represented by arrow 83, it is possible to identify a normal renal tubule and a glomerulus amyloid deposition. The glomerulus with amyloid with deposition is a cause of proteinuria and nephrotic syndrome, and its progression may cause chronic renal failure. Thus, in Embodiment 4, it is possible to identify tissue at risk of chronic renal failure before the chronic renal failure occurs, i.e., it is possible to identify tissue in which there is an abnormality. It is considered that it is also possible to identify whether there is amyloid deposition or not before the onset of a symptom (in the early stage) similarly in every organ of the body such as brain, heart, alimentary tract, liver, peripheral nerve, tongue, thyroid, and skin.

Software Implementation Example

Control blocks of the control section 31 (particularly, the absorbance ratio calculating section 43, the organ determining section 44, and the identification information generating section 45) can be realized by a logic circuit (hardware) provided in an integrated circuit (IC chip) or the like or can be alternatively realized by software.

In the latter case, the control section 31 is realized as a computer that executes instructions of a tissue identification program that is software realizing the foregoing functions. The control section 31, for example, includes at least one processor, and is communicably connected to the storage section 33 which is a computer-readable storage medium storing the program. An object of the present invention can be achieved by the processor of the control section 31 reading and executing the program stored in the storage medium.

Examples of the processor encompass a central processing unit (CPU). Examples of the storage medium encompass a "non-transitory tangible medium" such as a read only memory (ROM), a tape, a disk, a card, a semiconductor memory, and a programmable logic circuit. The computer may further include a random access memory (RAM) or the like in which the program is loaded. Further, the program may be made available to the computer via any transmission medium (such as a communication network and a broadcast wave) which allows the program to be transmitted. Note that an aspect of the present invention can also be achieved in the form of a computer data signal in which the program is embodied via electronic transmission and which is embedded in a carrier wave.

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST 1, 1a biological tissue identification system (tissue identification system)
2 biological tissue identification system (tissue identification system)
3 endoscope system
10 light source (first light source)
18 light detector (first light receiving section)
21 image capturing section (second light receiving section)
41 light source control section
43 absorbance ratio calculating section (calculating section)
44 organ determining section (determining section)
45 identification information generating section
51 inspection optical fiber (first optical fiber)
54 illuminating optical fiber (second optical fiber)
70 illuminating light source (second light source)
100 laser light (inspection light)
200 illuminating light (visible light)
300 main pulse
301 subpulse

The invention claimed is:
1. A tissue identification device comprising:
 a computer comprising a control section including at least one processor communicably connected to a computer-readable storage medium to execute instructions of a tissue identification program, the control section comprising:
 a calculating section configured to acquire a first measured value and a second measured value and calculate a ratio of the first measured value to the second measured value or a reciprocal of the ratio; and
 an identification information generating section configured to generate identification information indicative of a type or a state of biological tissue by determining within which of a plurality of preset numerical ranges the ratio or the reciprocal calculated by the calculating section falls, wherein
 the first measured value is a transmittance, a reflectance, or an absorbance indicated by a transmitted portion of first inspection light transmitted through the biological tissue or a reflected portion of first inspection light reflected from the biological tissue,
 the second measured value is a transmittance, a reflectance, or an absorbance indicated by a transmitted portion of second inspection light transmitted through the biological tissue or a reflected portion of second inspection light reflected from the biological tissue, and
 the first inspection light and the second inspection light have respective different peak wavelengths in a range of from 2 μm to 20 μm, inclusive, the tissue identification device further comprising:
- a determining section configured to determine from which organ the biological tissue is derived or determine which type or state is a candidate for the type or the state of the biological tissue, by comparing (i) a spectrum of a transmittance, a reflectance, or an absorbance indicated by light transmitted through the biological tissue or light reflected from the biological tissue and (ii) pre-stored spectra for a plurality of pieces of tissue derived from a plurality of types of organs or pre-stored spectra for a plurality of types of tissue in an organ; and
- a light source control section configured to control a light source, which is configured to emit the first inspection light and the second inspection light, to emit the first inspection light and the second inspection light that correspond to the organ or the candidate determined by the determining section,
- wherein the first measured value obtained by applying the first inspection light to the biological tissue differs depending on the type or the state of the biological tissue to a greater extent than the extent to which the second measured value obtained by applying the second inspection light to the biological tissue differs depending on the type or the state of the biological tissue, and
- wherein the light source control section controls the light source to oscillate the second inspection light having a reference wavelength associated with organ information that identifies the organ and the first inspection light having a discrimination wavelength associated with the organ information.

2. The tissue identification device as set forth in claim 1, wherein the identification information generating section is configured to generate identification information indicative of whether there is an abnormality in the biological tissue by determining within which of the plurality of preset numerical ranges the ratio or the reciprocal falls.

3. The tissue identification device as set forth in claim 1, wherein the identification information generating section is configured to generate identification information indicative of whether the biological tissue contains a tumor by determining within which of the plurality of preset numerical ranges the ratio or the reciprocal falls.

4. The tissue identification device as set forth in claim 3, wherein the identification information generating section is configured to generate identification information indicative of whether the tumor is benign or malignant by determining within which of the plurality of preset numerical ranges the ratio or the reciprocal falls.

5. The tissue identification device as set forth in claim 4, wherein the identification information generating section is configured to generate identification information indicative of the degree of malignancy of the tumor by determining within which of the plurality of preset numerical ranges the ratio or the reciprocal falls.

6. The tissue identification device as set forth in claim 1, wherein:
the calculating section is configured to calculate a plurality of the ratios or a plurality of the reciprocals with use of
- (i) a plurality of the first measured values obtained by applying, to the biological tissue, a plurality of types of the first inspection light having a plurality of peak wavelengths and (ii) the second measured value,
  - (a) the first measured value and (b) a plurality of the second measured values obtained by applying, to the biological tissue, a plurality of types of the second inspection light having a plurality of peak wavelengths, or
- (I) a plurality of the first measured values obtained by applying, to the biological tissue, a plurality of types of the first inspection light having a plurality of peak wavelengths and (II) a plurality of the second measured values obtained by applying, to the biological tissue, a plurality of types of the second inspection light having a plurality of peak wavelengths; and the identification information generating section is configured to generate identification information indicative of the type or the state of the biological tissue based on results obtained by determining within which of a plurality of preset numerical ranges each of the plurality of ratios or each of the plurality of reciprocals falls.

7. A computer-readable storage medium in which a tissue identification program is stored, the tissue identification program being a tissue identification program for causing a computer to function as a tissue identification device recited in claim 1 and causing the computer to function as the calculating section and the identification information generating section.

8. A tissue identification system comprising:
- a tissue identification device recited in claim 1;
- a light source configured to apply the first inspection light and the second inspection light to the biological tissue; and
- a light detector configured to measure (i) an intensity of transmitted light or reflected light resulting from application of the first inspection light and (ii) an intensity of transmitted light or reflected light resulting from application of the second inspection light.

9. The tissue identification system as set forth in claim 8, wherein the light source is a laser light source which is configured to oscillate laser light serving as the first inspection light and oscillate laser light serving as the second inspection light.

10. The tissue identification device as set forth in claim 1, wherein the first inspection light and the second inspection light have respective different peak wavelengths in a range of from 8 μm to 20 μm, inclusive.

11. The tissue identification device as set forth in claim 1, wherein the first inspection light and the second inspection light have respective different peak wavelengths in a range of from 2 μm to 11 μm, inclusive.

12. The tissue identification system as set forth in claim 8, wherein: the biological tissue is divided into segments each having a size of not smaller than 70 μm×70 μm and not larger than 500 μm×500 μm; and the absorbance is measured on a per-segment basis.

13. The tissue identification system as set forth in claim 8, wherein: the biological tissue is divided into segments each having a size of not larger than 70 μm×70 μm; and the absorbance is measured on a per-segment basis.

14. The tissue identification system as set forth in claim 8, wherein the light source is configured to selectively oscillate mid-infrared light having a specific peak wavelength and is capable of switching wavelengths.

15. The tissue identification system as set forth in claim 8, further comprising a condenser lens configured to focus the first inspection light and the second inspection light emitted from the light source to 10 μm or less in diameter.

16. The tissue identification system as set forth in claim 8, further comprising an objective mirror configured to focus the first inspection light and the second inspection light emitted from the light source.

17. The tissue identification system as set forth in claim 8, further comprising a display section configured to display, as an image, a result of identification of the biological tissue.

18. A method of identifying tissue carried out by a tissue identification device, the method comprising the steps of:
acquiring a first measured value and a second measured value, the first measured value being indicative of a transmittance, a reflectance, or an absorbance indicated by a transmitted portion of first inspection light transmitted through biological tissue or a reflected portion of the first inspection light reflected from the biological tissue, the second measured value being indicative of a transmittance, a reflectance, or an absorbance indicated by a transmitted portion of second inspection light transmitted through the biological tissue or a reflected portion of the second inspection light reflected from the biological tissue, the first inspection light and the second inspection light having respective different peak wavelengths in a range of from 2 μm to 20 μm, inclusive, wherein the first measured value obtained by applying the first inspection light to the biological tissue differs depending on the type or the state of the biological tissue to a greater extent than the extent to which the second measured value obtained by applying the second inspection light to the biological tissue differs depending on the type or the state of the biological tissue;
calculating a ratio of the first measured value to the second measured value or a reciprocal of the ratio; and
outputting identification information to an output device, the identification information being information that is generated by determining within which of a plurality of preset numerical ranges the ratio or the reciprocal falls and that is indicative of a type or a state of the biological tissue,
determining from which organ the biological tissue is derived or determining which type or state is a candidate for the type or the state of the biological tissue, by comparing (i) a spectrum of a transmittance, a reflectance, or an absorbance indicated by light transmitted through the biological tissue or light reflected from the biological tissue and (ii) pre-stored spectra for a plurality of pieces of tissue derived from a plurality of types of organs or pre-stored spectra for a plurality of types of tissue in an organ;
controlling a light source, which is configured to emit the first inspection light and the second inspection light, to emit the first inspection light and the second inspection light that correspond to the organ or the candidate determined in the step of determining, and
controlling the light source to oscillate the second inspection light having a reference wavelength associated with organ information that identifies the organ and the first inspection light having a discrimination wavelength associated with the organ information.

19. A tissue identification device comprising:
a computer comprising a control section including at least one processor communicably connected to a computer-readable storage medium to execute instructions of a tissue identification program, the control section comprising:
a calculating section configured to acquire a first measured value and a second measured value and calculate a ratio of the first measured value to the second measured value or a reciprocal of the ratio; and
an identification information generating section configured to generate identification information indicative of a type or a state of biological tissue by determining within which of a plurality of preset numerical ranges the ratio or the reciprocal calculated by the calculating section falls, wherein:
the first measured value is a transmittance, a reflectance, or an absorbance indicated by a transmitted portion of first inspection light transmitted through the biological tissue or a reflected portion of first inspection light reflected from the biological tissue;
the second measured value is a transmittance, a reflectance, or an absorbance indicated by a transmitted portion of second inspection light transmitted through the biological tissue or a reflected portion of second inspection light reflected from the biological tissue; and
the first inspection light and the second inspection light have respective different peak wavelengths in a range of from 2 μm to 20 μm, inclusive, and
wherein:
in a case where the biological tissue is lung tissue and whether the lung tissue is normal tissue or cancer tissue is determined, the first inspection light has a peak wavelength in a range of from 8.06 μm to 8.70 μm or in a range of from 8.75 μm to 10.05 μm;
in a case where the biological tissue is mammary tissue and whether the mammary tissue is normal tissue, adenoma, fibroadenoma, or cancer tissue is determined, the first inspection light has a peak wavelength in a range of from 9.80 μm to 10.60 μm, in a range of from 8.05 μm to 8.15 μm, in a range of from 8.22 μm to 8.62 μm, in a range of from 8.71 μm to 8.85 μm, or in a range of from 8.88 μm to 10.6 μm;
in a case where the biological tissue is liver tissue and whether the liver tissue is normal tissue or histiocytic sarcoma is determined, the first inspection light has a peak wavelength in a range of from 9.33 μm to 9.64 μm,
in a case where the biological tissue is liver tissue and whether the liver tissue is hepatocellular cancer or a lymphocyte is determined, the first inspection light has a peak wavelength in a range of from 8.05 μm to 8.40 μm or in a range of from 8.85 μm to 9.56 μm;
in a case where the biological tissue is tissue of muscle and bone and whether the tissue is normal tissue of muscle, normal tissue of bone, or cancer tissue of bone is determined, the first inspection light has a peak wavelength in a range of from 8.05 μm to 10.5 μm;
in a case where the biological tissue is cerebellar tissue and whether the cerebellar tissue is normal tissue or cancer tissue is determined, the first inspection light has a peak wavelength in a range of from 8.05 μm to 10.5 μm;
in a case where the biological tissue is liver tissue and whether the liver tissue is normal tissue or malignant lymphoma is determined, the first inspection light has a peak wavelength in a range of from 9.07 μm to 9.77 μm or in a range of from 9.82 μm to 10.8 μm;
in a case where the biological tissue is muscle tissue and whether the muscle tissue is normal tissue or cancer tissue is determined, the first inspection light has a peak wavelength in a range of from 8.20 μm to 8.66 μm or in a range of from 8.91 μm to 11.0 μm;
in a case where the biological tissue is spleen tissue and whether the spleen tissue is normal tissue or cancer tissue is determined, the first inspection light has a peak wavelength in a range of from 8.05 μm to 8.39

µm, in a range of from 8.70 µm to 9.58 µm, or in a range of from 9.87 µm to 10.9 µm;

in a case where whether the biological tissue is tissue of bone marrow, rhabdomyosarcoma, muscle, or bone is determined, the first inspection light has a peak wavelength in a range of from 8.87 µm to 9.02 µm;

in a case where the biological tissue is liver tissue and whether the liver tissue is normal tissue, cancer tissue, or a lymphocyte is determined, the first inspection light has a peak wavelength in a range of from 9.10 µm to 9.55 µm;

in a case where the biological tissue is lung tissue and whether the lung tissue is normal tissue, primary lung cancer tissue, or a lesion of pulmonary metastasis of liver cancer is determined, the first inspection light has a peak wavelength in a range of from 9.75 µm to 10.00 µm;

in a case where the biological tissue is heart tissue and whether the heart tissue is normal tissue or a cardiac infarct area is determined, the first inspection light has a peak wavelength in a range of from 9.18 µm to 9.71 µm or in a range of from 9.84 µm to 11.00 µm;

in a case where the biological tissue is liver tissue and whether the liver tissue is normal tissue or tissue of fatty liver is determined, the first inspection light has a peak wavelength in a range of from 8.05 µm to 9.18 µm, in a case where the biological tissue is liver tissue and whether the liver tissue is normal tissue or tissue of liver cirrhosis is determined, the first inspection light has a peak wavelength in a range of from 8.61 µm to 9.00 µm or in a range of from 9.05 µm to 9.26 µm;

in a case where the biological tissue is cerebellar tissue and whether the cerebellar tissue is normal tissue, radiation-induced cancer tissue, or spontaneous cancer tissue is determined, the first inspection light has a peak wavelength in a range of from 8.80 µm to 9.34 µm or in a range of from 9.89 µm to 10.25 µm; or in a case where the biological tissue is kidney tissue and whether the kidney tissue is a normal renal tubule or a glomerulus with amyloid deposition is determined, the first inspection light has a peak wavelength in a range of from 8.88 µm to 9.14 µm;

wherein the first measured value obtained by applying the first inspection light to the biological tissue differs depending on the type or the state of the biological tissue to a greater extent than the extent to which the second measured value obtained by applying the second inspection light to the biological tissue differs depending on the type or the state of the biological tissue, and wherein the first inspection light and the second inspection light each have a wavelength corresponding to a type or state of biological tissue.

* * * * *